(12) United States Patent
Yumikino

(10) Patent No.: US 7,364,557 B2
(45) Date of Patent: Apr. 29, 2008

(54) JOINT COUPLING FOR PROSTHETIC BRACE

(75) Inventor: Yuji Yumikino, Kagoshima (JP)

(73) Assignee: Izumi Gishi Sougu Seisakusho Co., Ltd., Kagoshima (JP)

( * ) Notice: Subject to any disclaimer, the term of this patent is extended or adjusted under 35 U.S.C. 154(b) by 215 days.

(21) Appl. No.: 11/124,344

(22) PCT Filed: Oct. 19, 2004

(86) PCT No.: PCT/JP2004/015425

§ 371 (c)(1),
(2), (4) Date: Jun. 27, 2005

(87) PCT Pub. No.: WO2005/039459

PCT Pub. Date: May 6, 2005

(65) Prior Publication Data

US 2005/0276657 A1 Dec. 15, 2005

(30) Foreign Application Priority Data

Oct. 22, 2003 (JP) ............................. 2003-361600
May 20, 2004 (JP) ............................. 2004-002833

(51) Int. Cl.
*A61F 5/00* (2006.01)

(52) U.S. Cl. ............................. 602/16; 602/26; 602/27; 602/19; 602/20

(58) Field of Classification Search .................. 602/16, 602/26

See application file for complete search history.

(56) References Cited

U.S. PATENT DOCUMENTS 5,074,290 A * 12/1991 Harris et al. .................. 602/16
5,244,455 A * 9/1993 Swicegood et al. ........... 602/16
2005/0101887 A1* 5/2005 Stark et al. ..................... 601/5

FOREIGN PATENT DOCUMENTS

JP 63-193012 12/1988

* cited by examiner

*Primary Examiner*—Patricia Bianco
*Assistant Examiner*—Tarla Patel
(74) *Attorney, Agent, or Firm*—Jordan and Hamburg LLP

(57) ABSTRACT

A compact joint coupling for a prosthetic brace can maintain a fixed state and can accommodate bending motion of the brace. A rotor having a recessed groove formed therein is rotatably mounted on a central shaft between a first coupling base and a second coupling base. Protruding pieces on the second coupling base are adapted to fit slidably within the groove. In addition, the surface of the second coupling base is covered with a cover for operating an operation pin. The groove is adapted to hold a plurality of spheres. The spheres can be manually introduced into, and removed from, the groove. The spheres are adapted to slide within the groove as the brace is bent. A purpose of the spheres is to prevent the brace from being bent by more than a predetermined amount.

7 Claims, 35 Drawing Sheets

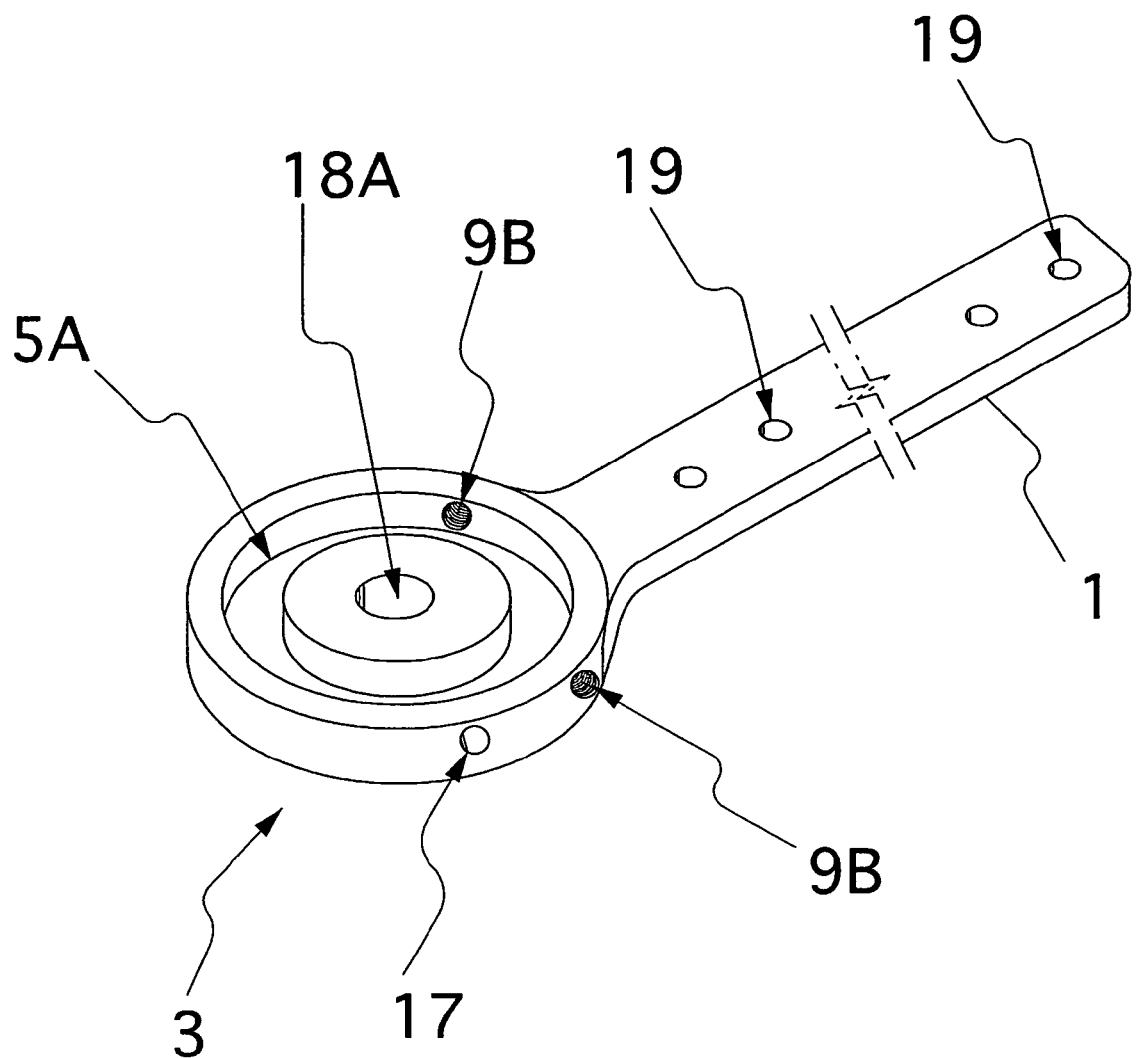
F I G.3

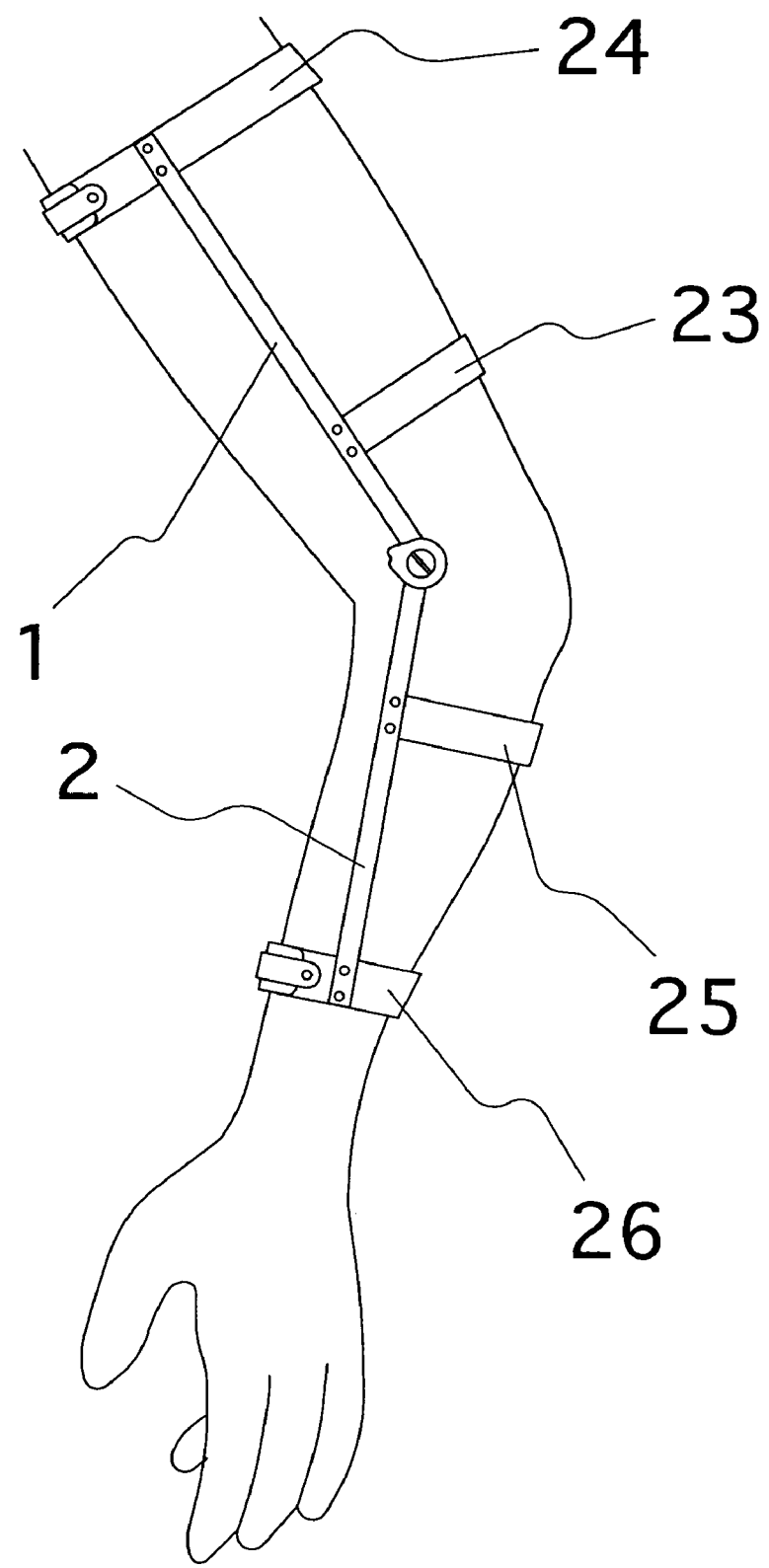
F I G . 10

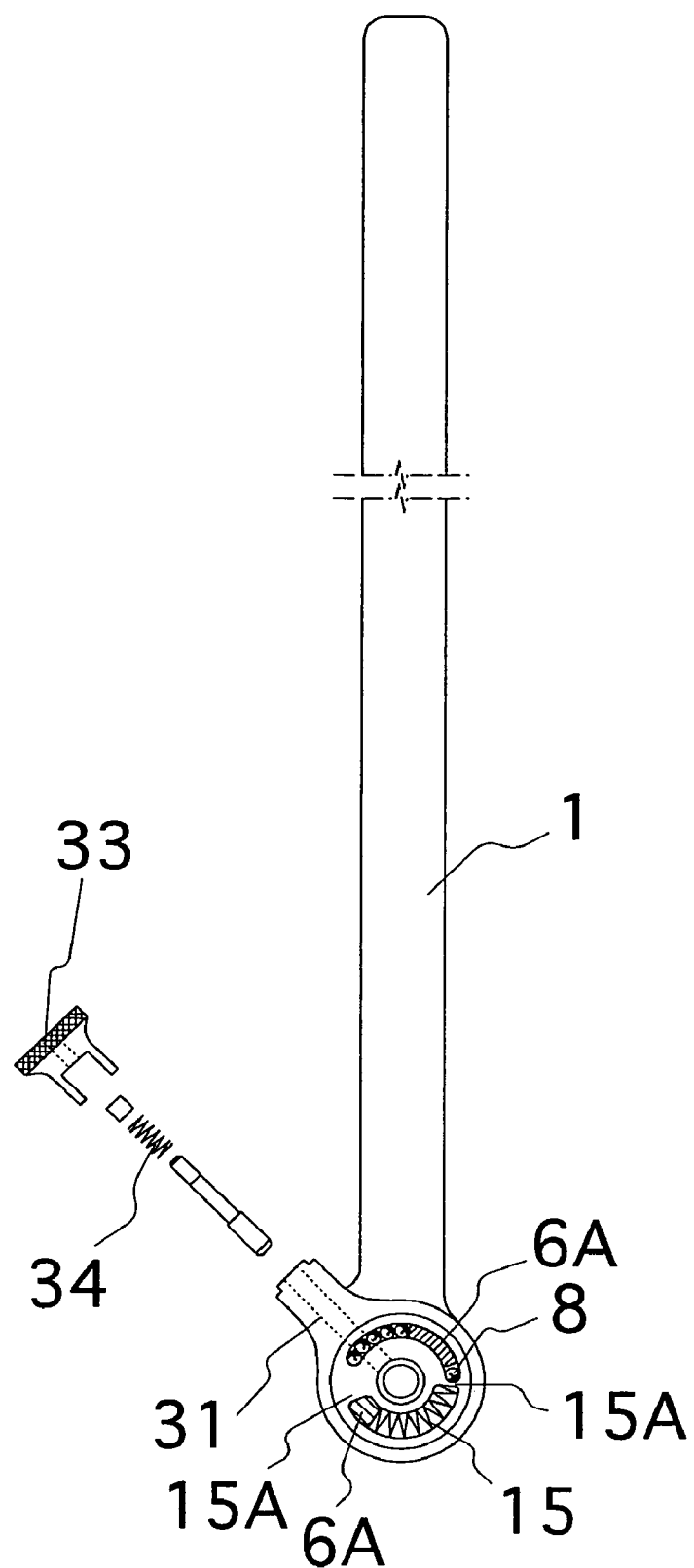
F I G .12

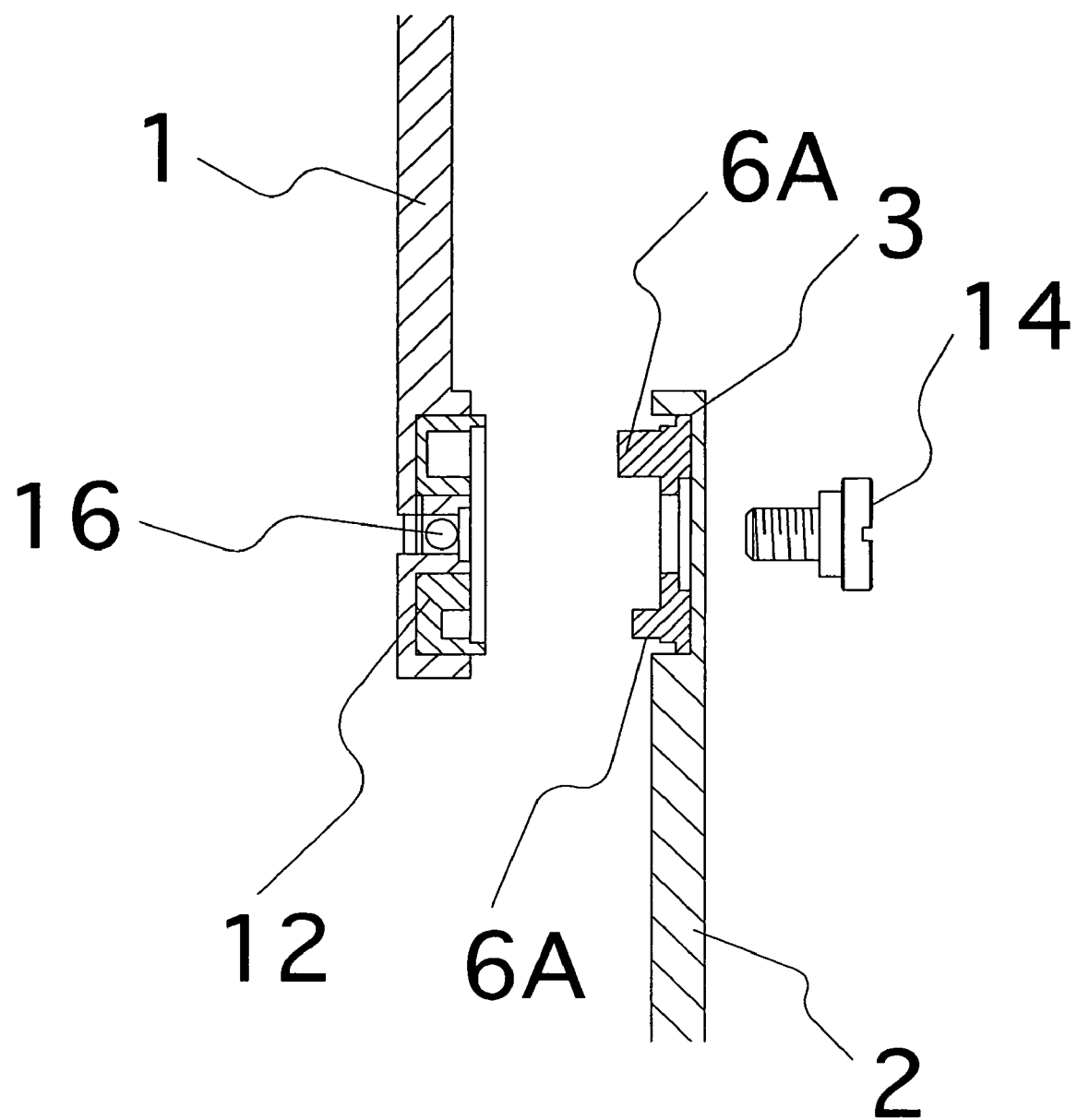
F I G.14

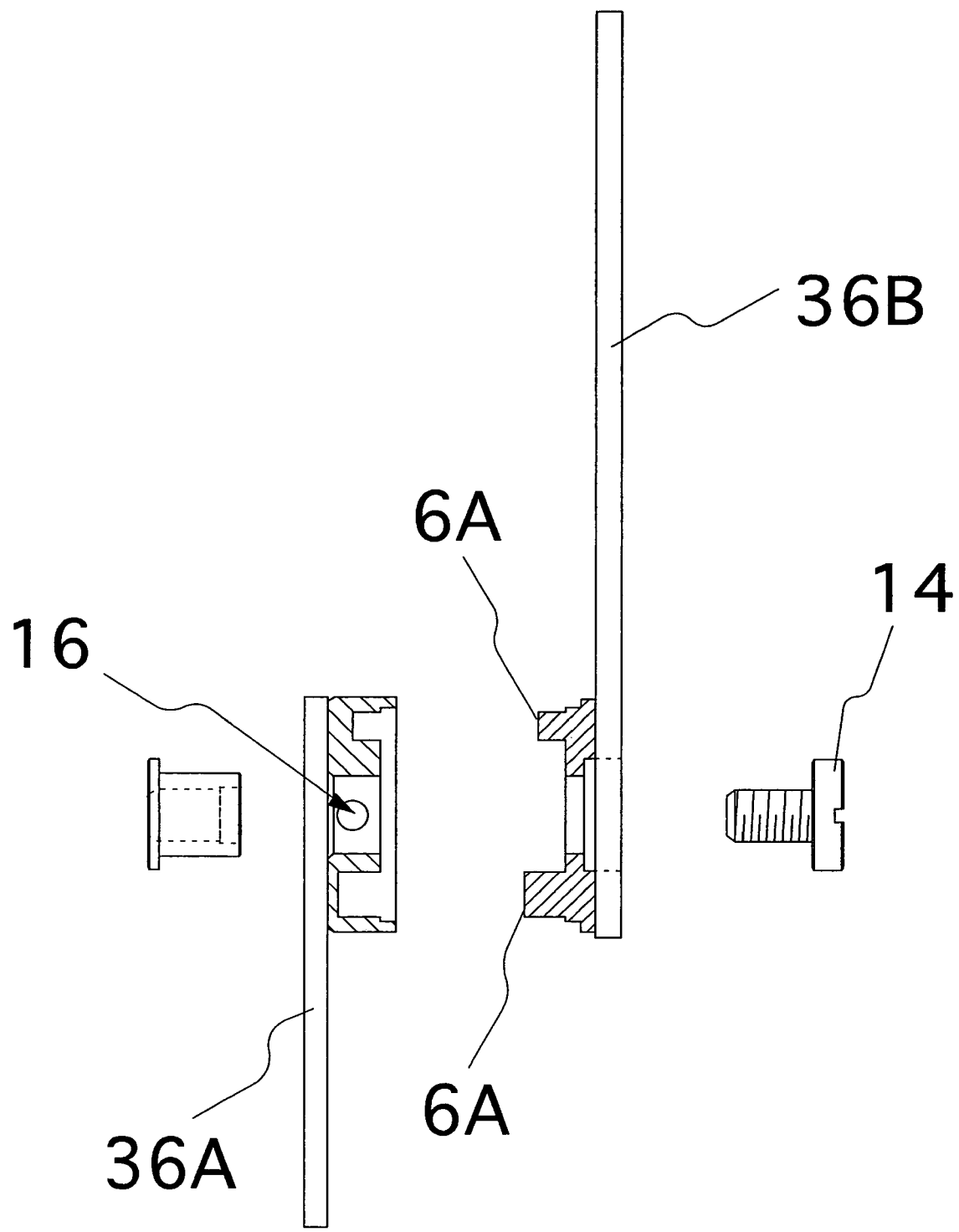
F I G.19

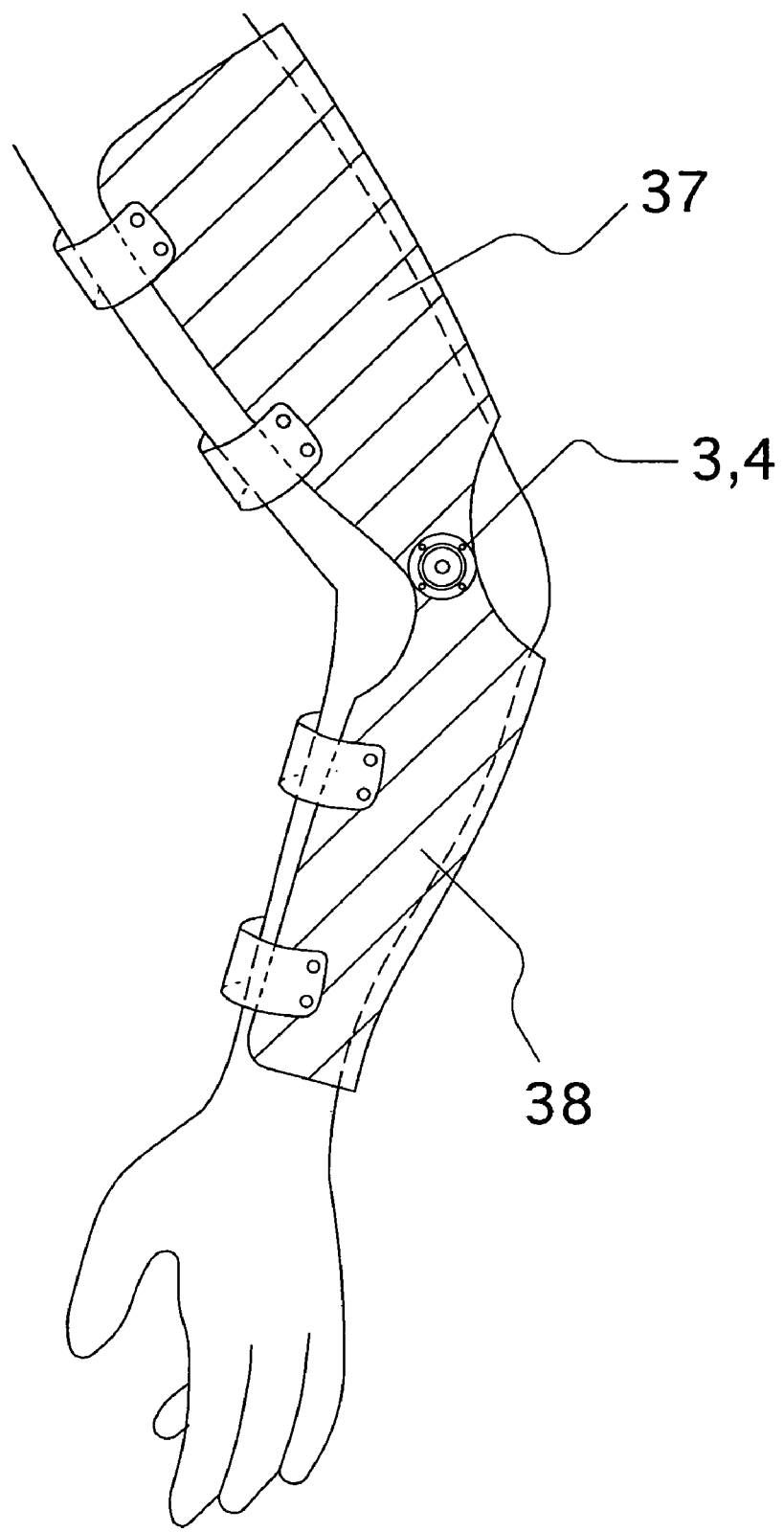
F I G.20

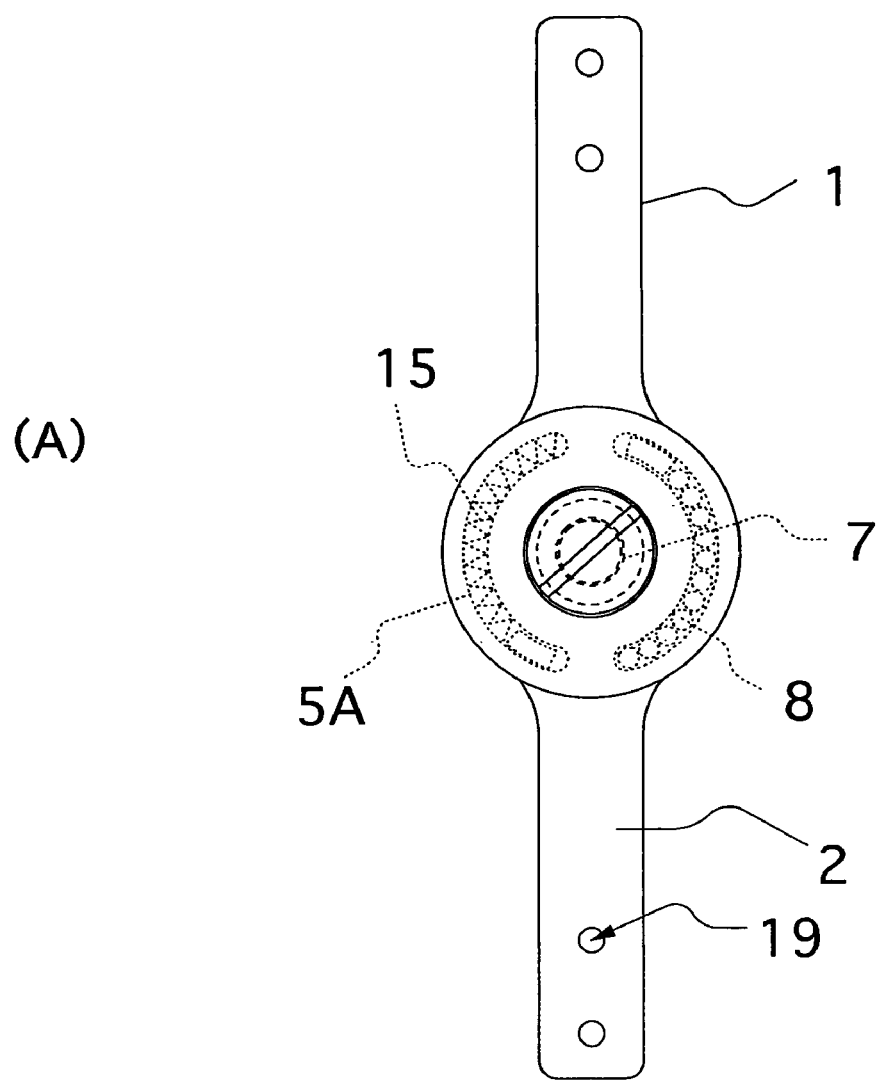
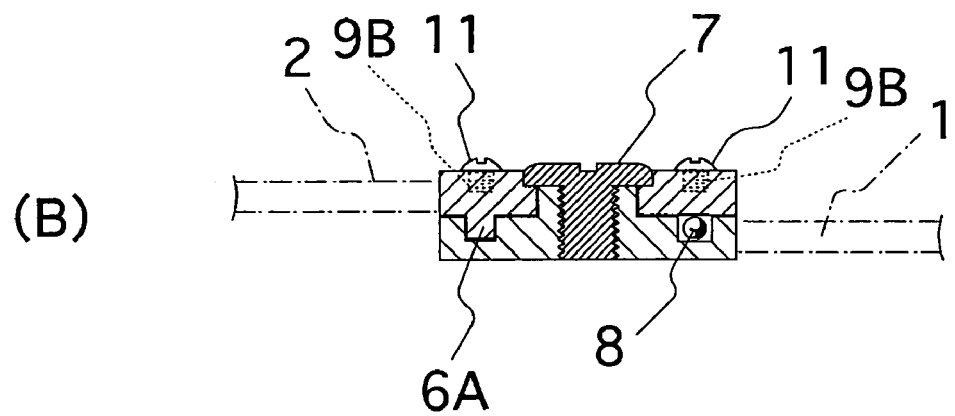
F I G. 24

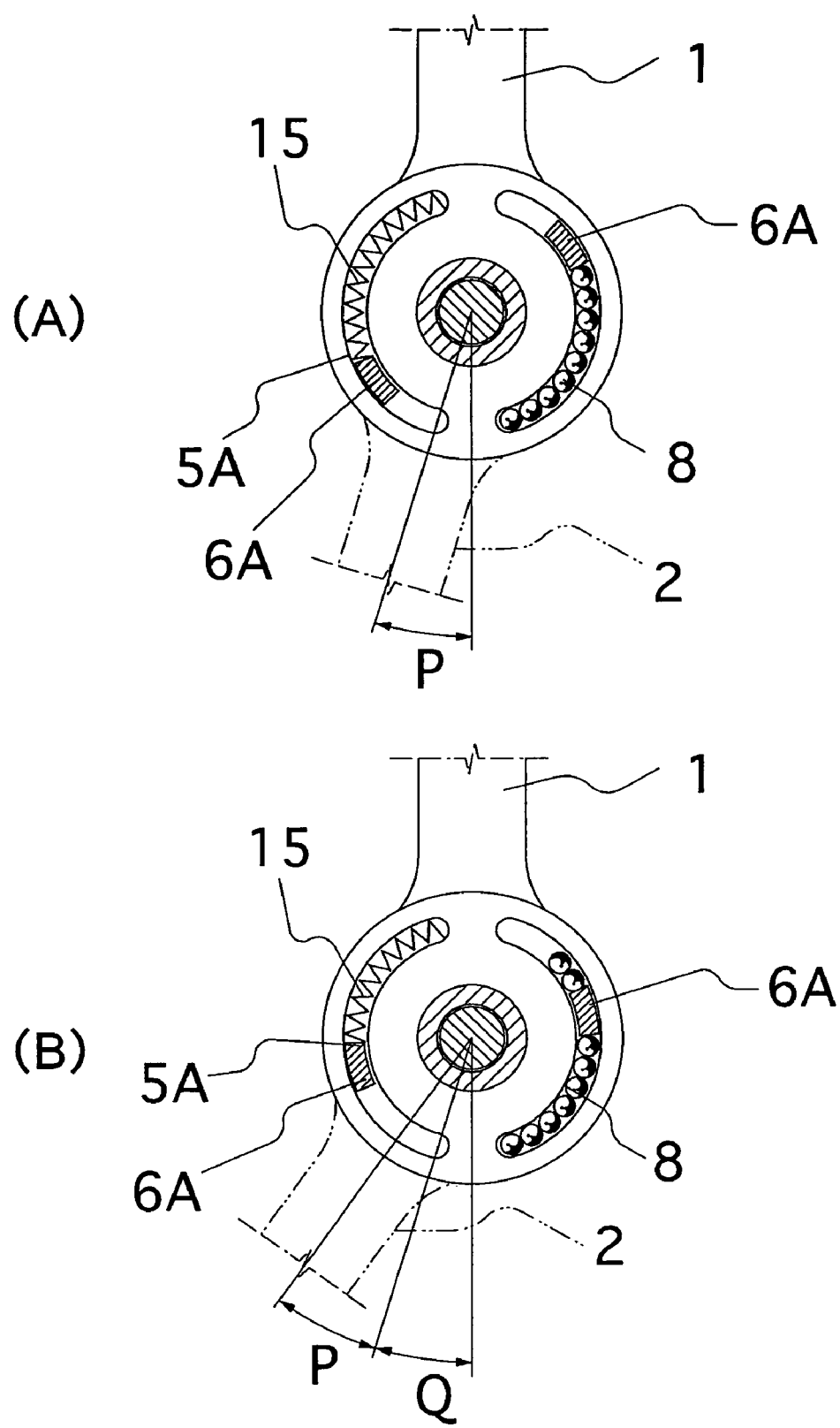
F I G. 27

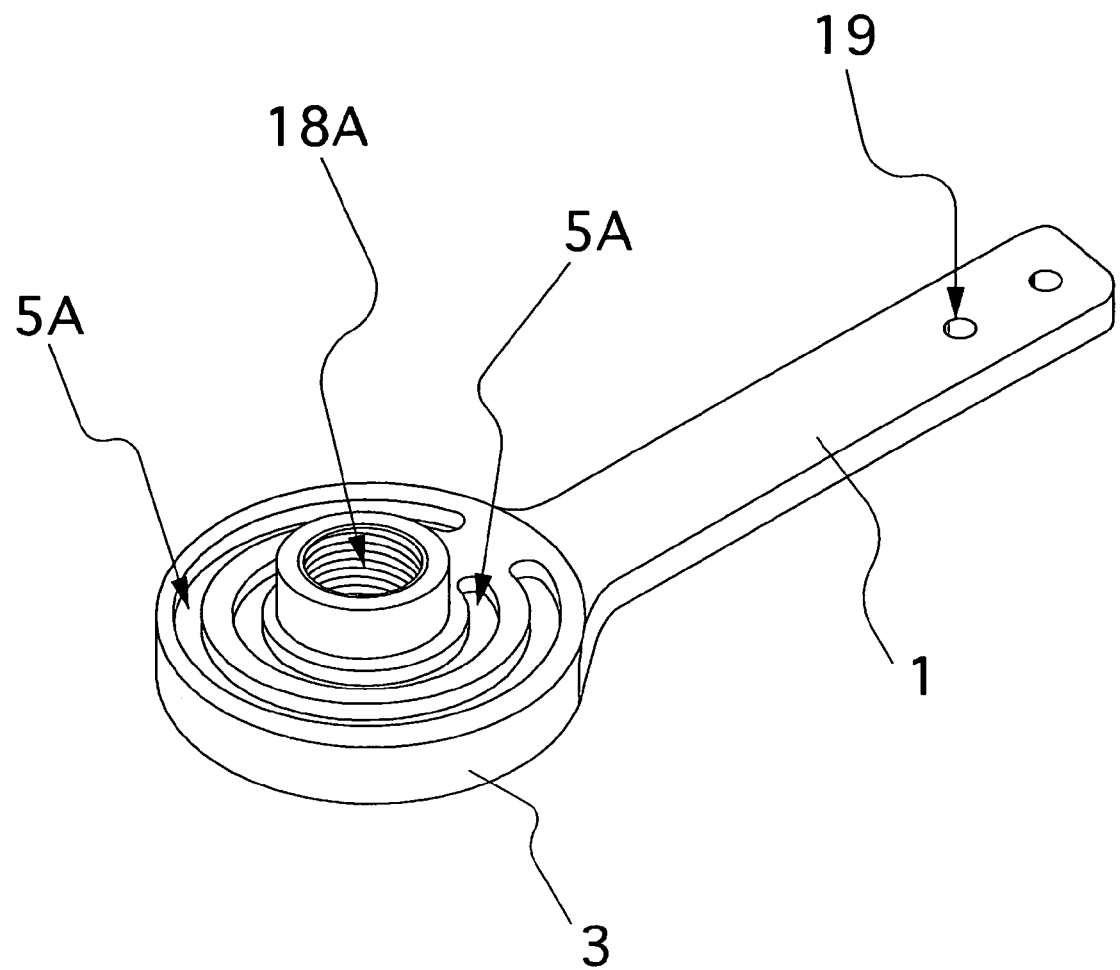
F I G. 29

JOINT COUPLING FOR PROSTHETIC BRACE

TECHNICAL FIELD

The present invention relates to a joint coupling for a prosthetic brace. More particularly, the present invention relates to the joint coupling for the prosthetic brace in a joint movable range training for improving the motion of a joint stiffened.

BACKGROUND ART

It is necessary for a person having a handicap in the body as a result of apoplexy, rheumatism and a traffic accident or the like to perform a muscular power reinforcement training of muscles which have become weak by paralysis or being bedridden, a joint movable region training for improving the motion of the stiffened joint by articular rheumatism or by not moving after an operation, a basic motion such as rolling over, rising and standing up, and the practice of walking in order that the person returns to home or society and becomes independent.

The joint coupling is used for the prosthetic brace in the joint movable range training. Although a fixed type joint coupling which does not have a movable region, and a joint coupling for deducing at intervals of a fixed angle, setting by using a bolt or the like and performing a movable region training are available commercially, it is necessary to exchange to the joint coupling for performing the movable region training from the fixed type joint coupling as the motion of the stiffened joint by the movable region training is improved.

The following joint coupling is disclosed. The upper end of a lower brace (coupling rod) and the lower end part of an upper brace (coupling rod) are pivoted at the central part of a disk-like substrate via an arm plate in order to integrate the fixed type joint coupling and the movable region training type joint coupling. A great number of screw holes are formed on the periphery of the disk-like substrate, and the lower brace is fixed by fixed screws from the screw holes provided at the lower brace, and a pair of left and right screws for movable restriction are screwed into the screw holes of the substrate on left-and-right both sides of the lower brace. The movable training is performed within the movable restriction region of the screws. A ring block is fitted by connecting the arm plate to the lower end part of the upper brace, and the lower end edge part of the ring block is locked in a groove formed on the upper end of the disk-like substrate by sliding the ring block downwards. Thereby, the arm plate and the disk-like substrate are fixed. The upper brace and the lower brace are fixed by stopping the disk-like substrate using the lower brace and the fixed screw in the state where the arm plate and the disk-like substrate are fixed. The upper brace and the lower brace are fixed by removing the fixed screw. The lower brace can be moved within a pair of left and right screws for movable restriction and the movable restriction region of the screws by removing the fixed screw, and the movable region training can be performed (for example, see Patent Document 1).

Patent Document 1: Japanese Published Unexamined Utility Model Application No. S63-193012

DISCLOSURE OF THE INVENTION

Problems to be Solved by the Invention

However, in the joint coupling having the above constitution, since the bending angle of the lower brace (coupling rod) is deduced and is fixed by opening the screw holes on the periphery of the disk-like substrate, and stopping using the fixed screw, for example, a great number of screw holes of a plurality of rows must be mutually opened on the periphery of the disk-like substrate with an angle difference in order to reduce and deduce the bending angle. The size of the disk-like substrate becomes larger, and thereby it is hard to apply to joints for small joints. Also, the joint coupling cannot be bent at the angle which can be applied to sitting straight on the structure.

One pair of right and left screws for movable restriction are screwed into the movable restriction region, and the movable region training is repeatedly performed while the left-and-right both sides of the lower brace are applied within the restriction region between the screws. Thereby, the screws are loosened and easily fall out, and it is necessary to consider safety. Clothing is caught on the groove for locking the ring block provided on the upper end of the substrate, and the clothing is damaged.

The present invention has been accomplished in view of the foregoing and other problems. It is an object of the present invention to provide the joint coupling for the prosthetic brace capable of adjusting the movable region of the joint freely by taking in and out the spheres.

Means for Solving the Problems

To attain the above object, the joint coupling for the prosthetic brace according to the present invention, comprises: a first coupling base having a recessed groove in which spheres are arrayed and charged along the circumference; a second coupling base which has a protruding piece fitted to the recessed groove and protrusively formed on the circumferential surface, and rotatably pivots the first coupling base by the central shaft; and an operation pin which is freely insertable in the recessed groove by a suitable means and controls the movement of the spheres charged in the recessed groove.

Herein, the first coupling base having the recessed groove in which the spheres are arrayed and charged along the circumference, and the second coupling base having the protruding piece fitted to the recessed groove and protrusively formed on the circumferential surface are pivoted by the central shaft. The protruding piece is made to go around in the groove part by charging the spheres in the recessed groove, and thereby the spheres charged are revolved in the recessed groove when the coupling bases are mutually rotated, and the coupling bases can be smoothly rotated. Then, the rotation of the coupling bases can be stopped by inserting an operation pin into the recessed groove using a suitable means to stop the spherical revolution. In this case, a gap is generated in the recessed groove by the number of spheres charged in the recessed groove, and the gap can adjust the movable region of the coupling base.

To attain the above object, the joint coupling for the prosthetic brace according to the present invention, comprises: a first coupling base rotatably intruding a rotor having a plurality of recessed grooves in which spheres are arrayed and charged along the circumference; a second coupling base which has a protruding piece fitted to the recessed groove of the rotor and protrusively formed on the circumferential surface, and rotatably pivots the first coupling base in the state where the rotor is interposed by the central shaft; and an operation pin for locking the rotation of the rotor to the first coupling base by using a suitable means.

Herein, the rotor is pivoted in the state where the rotor in which a plurality of recessed grooves in which the spheres are arrayed and charged along the circumference are formed can be freely rotated to the first coupling base. The second coupling base in which the protruding piece fitted to the recessed groove of the rotor is protrusively formed on the circumferential surface is pivoted in the state where the second coupling base can be freely rotated by the central shaft. The operation pin for locking the rotation of the rotor by a suitable means is provided. Therefore, in the state where the rotation of the rotor is locked, the protruding piece of the second coupling base fitted to the recessed groove is rotated by the gap in the recessed groove due to the number of spheres charged in the recessed groove. The movable region of the coupling base can be adjusted by taking in and out the spheres. The operation pin releases the locking of the rotor, and the rotor is rotated. The second coupling base integrally formed with the protruding piece fitted to the recessed groove of the rotor can also be rotated similarly.

In addition, the spheres are charged in one split recessed groove, and the freely expansible and contractible elastic member is attached to the other recessed groove. Thereby, the coupling base attached as an artificial joint of a prosthesis or a brace generates the action for restoring to the original position by the restitution of the elastic member to the bending of a hand and leg within the movable region.

To attain the above object, the joint coupling for the prosthetic brace according to the present invention, comprises: a first coupling base having a recessed groove in which spheres are arrayed and charged along the circumference; and a second coupling base which has a protruding piece fitted to the recessed groove and protrusively formed on the circumferential surface, and rotatably pivots the first coupling base by the central shaft, wherein the rotation of the second coupling base is controlled by abutting against the protruding piece provided on the second coupling base on the spheres charged in the recessed groove.

Herein, the second coupling base in which the protruding piece fitted to the recessed groove is provided is rotatably pivoted to the first coupling base having the recessed groove in which the spheres are arrayed and charged along the circumference. The gap is generated in the recessed groove by adjusting the number of spheres charged in the recessed groove, and the gap can adjust the movable region of the second coupling base.

To attain the above object, the joint coupling for the prosthetic brace according to the present invention, comprises: a first coupling base having a plurality of recessed grooves formed along the circumference; and a second coupling base which has a protruding piece fitted to the recessed groove of the first coupling base and protrusively formed on the circumferential surface, and rotatably pivots the first coupling base in the state where the rotor is interposed by the central shaft, wherein the spheres are charged in one split recessed groove of the first coupling base, and a freely expansible and contractible elastic member is attached in the other split recessed groove.

Herein, the second coupling base in which the protruding piece of the first coupling base fitted to the recessed groove, respectively, is protrusively formed on the circumferential surface is rotatably pivoted to the first coupling base in which the recessed groove is substantially half-split to the left and right along the circumference. The gap is generated in the recessed groove by charging the spheres in one recessed groove, attaching the freely expansible and contractible spring to the other recessed groove, and adjusting the number of spheres charged in the recessed groove. The gap can adjust the movable region of the second coupling base, and the action for restoring to the original position by the restitution of the spring to rotation of the second coupling base is generated.

To attain the above object, the joint coupling for the prosthetic brace according to the present invention, comprises: a first coupling base having two-row recessed grooves formed along the circumference; and a second coupling base which has a protruding piece fitted to each recessed groove of the first coupling base and protrusively formed on the circumferential surface, and rotatably pivots the first coupling base in the state where the rotor is interposed by the central shaft, wherein the spheres are charged in the recessed groove of the first row of the first coupling base, and a freely expansible and contractible elastic member is attached in the recessed groove of the second row.

Herein, the second coupling base in which the protruding piece of the first coupling base fitted to the recessed groove, respectively, is protrusively formed on the circumferential surface is rotatably pivoted to the first coupling base in which two-row recessed grooves are formed along the circumference. The spheres are charged in the recessed groove of the first row, and a freely expansible and contractible spring is attached into the recessed groove of the second row. The gap is generated in the recessed groove by adjusting the number of spheres charged in the recessed groove, and the gap can adjust the movable region of the second coupling base, and the action for restoring to the original position by the restitution of the spring to rotation of the second coupling base is generated.

The movable region suitable for the patient can be adjusted by providing a mechanism for taking in and out the spheres of the recessed groove from the first coupling base or the second coupling base and by adjusting the number of spheres charged in the recessed groove.

Effects of the Invention

In the joint coupling for the prosthetic brace of the present invention having the above constitution, for example, when the first coupling base is fixed to the prosthesis or brace of a movable side and the second coupling base is fixed to the prosthesis or brace of the fixation side, the spheres arrayed and charged in the recessed groove of the circumference formed on the first coupling base are stopped by operating the operation pin, and the protruding piece provided in the second coupling base is caught by the spheres. Thereby, the first coupling base can be fixed, and the gap due to the part of the number of extracted spheres is formed by extracting the spheres. The movable region training can be performed by moving the first coupling base within the range of the gap.

A deduction angle is deduced by the diameter of the sphere and the distance between the axial center rotatably pivoted and the center of the sphere arrayed and charged in the recessed groove of the circumference. The deduction angle can be reduced, and the effect for adjusting in the range in which the bending angle is small is exhibited. In addition, the effect for obtaining a simple and compact joint coupling is exhibited, and the joint coupling for the prosthetic brace can also be applied to a coupling for a small joint. The first coupling base is freely rotated by releasing the locking of the rotor due to the operation pin. The joint coupling can be folded up, and a leg joint coupling can also be applied to the case of sitting straight.

Since the protruding piece provided on the second coupling base is brought into contact with the spheres arrayed and charged in the recessed groove of the first coupling base to regulate the rotation of the first coupling base and the movable region training is performed, the movable region training is safely performed by hitting repeatedly without loosening and falling out in the same manner as a screw. In addition, since the unevenness is not formed on a joint exterior, there is no possibility that clothing may be caught and damaged at the time of attaching the coupling or the like.

In addition, since the spring force is added and the movable region training can be performed by attaching the freely expansible and contractible spring to the recessed groove, muscle power can be increased while the movable region training is performed.

Best Mode for Carrying Out the Invention

Now, with reference to the figures, embodiments of the present invention are detailed below, and understanding of the present invention is presented.

BRIEF DESCRIPTION OF THE DRAWINGS

FIG. 3 is a perspective view of an upper coupling rod of a joint coupling for a prosthetic brace according to Example 2 of the present invention.

FIG. 10 is an explanatory view showing the state where a prosthetic brace to which the present invention is attached is attached to an arm part.

FIG. 12 is an explanatory view of an upper coupling rod of a joint coupling for a prosthetic brace according to Example 3 of the present invention.

FIG. 14 is an enlarged sectional explanatory view of an essential part of a joint coupling for a prosthetic brace according to Example 3 of the present invention.

FIG. 19 is an assembling explanatory view of a joint coupling for a prosthetic brace according to Example 5 of the present invention.

FIG. 20 is an explanatory view showing the state where a joint coupling for a prosthetic brace according to Example 4 of the present invention is attached to an upper arm brace and a forearm brace.

FIG. 24 is an explanatory view of a joint coupling for a prosthetic brace according to the present invention.

FIG. 27 is a plane sectional explanatory view showing the example of a using form of a joint coupling for a prosthetic brace according to Example 7 of the present invention.

FIG. 29 is an explanatory view of a first coupling base of a joint coupling for a prosthetic brace according to Example 8 of the present invention.

DESCRIPTION OF THE PREFERRED EMBODIMENTS

EXAMPLE 1

Figure 1:
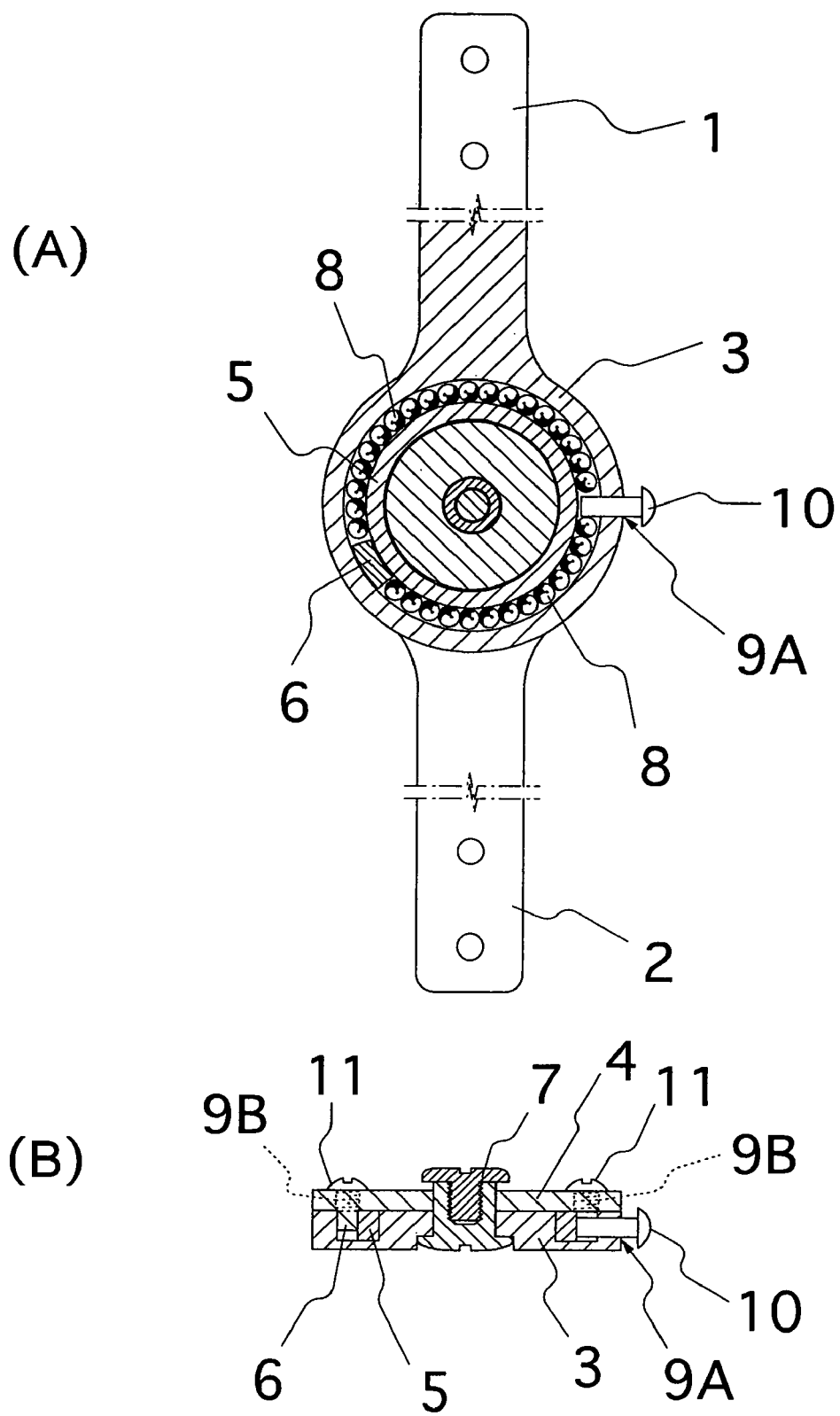
FIG. 1 is an illustration of a joint coupling for a prosthetic brace according to Example 1 of the present invention.

As shown in FIG. 1A and FIG. 1B, a disk-like first coupling base 3 and a second coupling base 4 are provided at a lower end part of a upper coupling rod 1 and a upper end part of a lower coupling rod 2. A recessed groove 5 is formed along the circumference of the first coupling base 3.

A protruding piece 6 fitted to the recessed groove 5 is formed on the circumferential surface of the second coupling base 4, and the first coupling base 3 and the second coupling base 4 are mutually pivoted in a rotatable state by a central shaft 7.

A plurality of spheres 8 formed of a superhard steel material are charged in the recessed groove 5 formed along the circumference of the first coupling base 3 in the state where the protruding piece 6 of the second coupling base 4 is sandwiched. A screw hole 9A communicated with the recessed groove 5 is bored on the outer peripheral edge of the first coupling base 3, and a screw-type operation pin 10 is screwed into the screw hole 9A. The operation pin 10 can block the recessed groove 5 to lock the rotation movement of the spheres 8, or can release the locking.

Two screw holes 9B having a diameter for freely taking in and out the spheres 8 are bored on the outer surface of the second coupling base 4 so that the screw holes 9B are communicated with the recessed groove 5. A lid screw 11 for blocking the screw hole 9B is screwed into the screw hole 9B.

Herein, for example, the upper coupling rod 1 as a fixation side and the lower coupling rod 2 as a movable side are attached to a prosthesis or a brace. When the recessed groove 5 is blocked by the operation pin 10 and the spheres 8 are charged in the state where a gap is not generated in the recessed groove 5, the rotation movement of the spheres 8 in the recessed groove 5 is stopped, and the rotation of the second coupling base 4 is locked. Next, a gap is generated between the spheres 8 by removing the lid screw 11 from this state and extracting the required number of spheres 8 charged in the recessed groove 5. The spheres 8 are is rotated and moved by the length of the gap, and the protruding piece 6 of the second coupling base 4 can be moved in the recessed groove 5. Therefore, the movable region of the second coupling base 4 can be set by taking in and out the spheres 8.

When the locking of the spheres 8 due to the operation pin 10 is released, the spheres 8 are also moved while being rotated in the recessed groove 5 while the protruding piece 6 of the second coupling base 4 is rotated in the recessed groove 5. The second coupling base 4 can be freely rotated by 360°.

EXAMPLE 2

Figure 2:
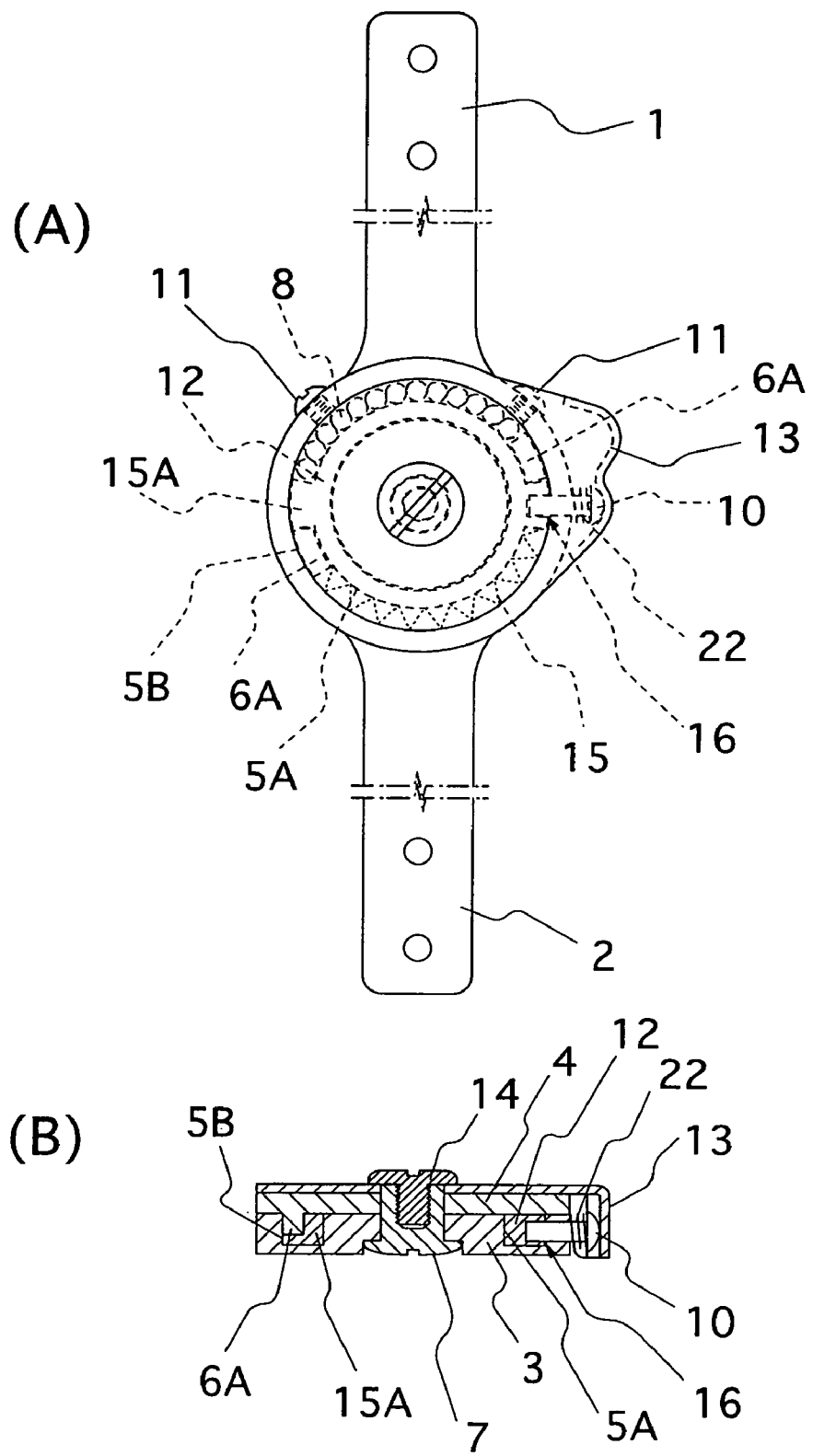
FIG. 2 is an illustration of a joint coupling for a prosthetic brace according to Example 2 of the present invention.

As shown in FIG. 2A and FIG. 2B, the disk-like first coupling base 3 and the second coupling base 4 are provided at the lower end part of the upper coupling rod 1 and the upper end part of the lower coupling rod 2. A recessed groove 5A is formed on the first coupling base 3. The rotor 12 is rotatably intruded into the recessed groove 5A, and a recessed groove 5B for arraying and charging the spheres is formed on the rotor 12 and the recessed groove 5A. Protruding pieces 6A and 6A provided on the circumferential surface of the second coupling base 4 of the lower coupling rod 2 are fitted to the recessed groove 5B. In addition, the surface of the second coupling base 4 is covered with an operation cover 13 for operating the operation pin 10. The first coupling base 3 and a second coupling base 4 are pivoted so as to be rotated by the central shaft 7 and a stopper screw 14 for preventing the escape of the central shaft 7.

Convex parts 15A and 15A are provided at two positions of the outer diameter part of the rotor 12, and the circumference of the recessed groove 5B for arraying and charging the spheres is bisected by the convex parts 15A and 15A. The spheres 8 are arrayed and charged in the recessed groove 5B of one bisected half, and a freely expansible and contractible spring 15 is attached to the recessed groove 5B of the other half. The operation pin 10 is taken in/out of a hole 16 formed on the convex part 15A of the outer diameter part of the rotor 12 from the side part of the first coupling base 3 by the operation of the operation cover 13, and thereby the rotor 12 can be stopped or can be freely rotated.

FIG. 3 is a perspective view of the upper coupling rod 1, and the disk-like first coupling base 3 is provided at the lower end part. So as to rotatably fit the rotor 12 to the first coupling base 3, the recessed groove 5A having a larger groove diameter than that of the sphere 8 charged is formed. The recessed groove 5B in which the spheres 8 are arrayed and charged is formed by the rotor 12 intruded and the recessed groove 5A. Screw holes 9B and 9B for taking in and out the spheres 8 of the recessed groove 5B, and an insertion hole 17 for inserting the operation pin 10 from the side part are bored. A bearing hole 18A for rotatably supporting the central shaft 7 is bored at the center of the first coupling base 3. Fitting holes 19 and 19 for attaching to the prosthetic brace are bored on the upper coupling rod 1.

The insertion hole 17 for inserting the operation pin 10 is bored on the side part of the first coupling base 3 of the 180° position of an opposite side at the time of assembling by locating the operation cover 13 at a position oppositely oriented for handling, the screw holes 9B and 9B are blocked by the lid screw 11 when the spheres 8 are not taken in and out.

Figure 4:
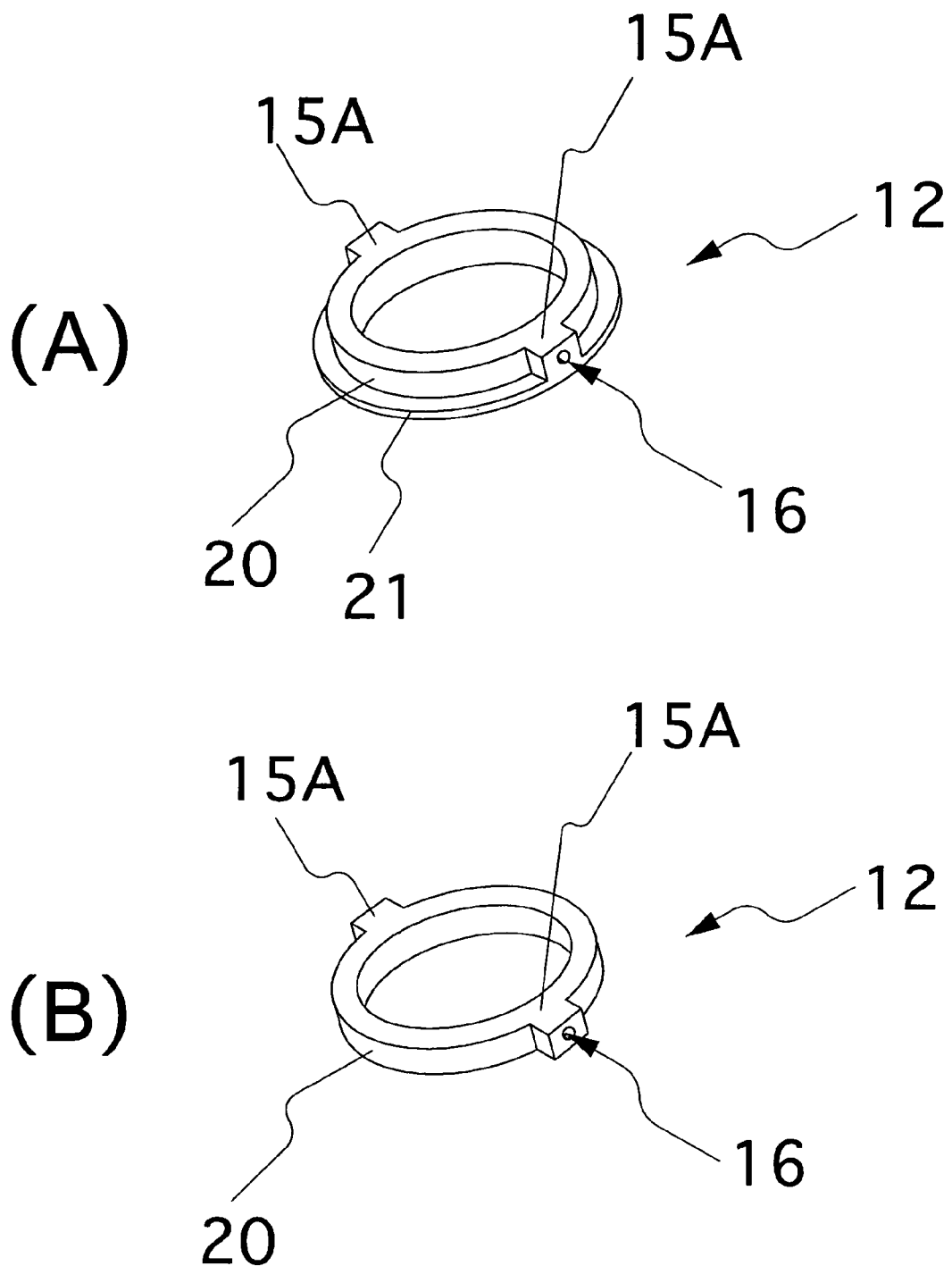
FIG. 4 is a perspective view of a rotor of a joint coupling for a prosthetic brace according to Example 2 of the present invention.

FIG. 4 is a perspective view of the rotor 12, and the convex parts 15A are formed at two positions of the outer diameter part 20 of the rotor 12. The hole 16 is formed on the side part of the convex part 15A, and the convex part 15A is rotatably fitted to the recessed groove 5A formed on the first coupling base 3, and the hole 16 coincides with the insertion hole 17 bored on the side part of the first coupling base 3 at the time of fitting. The tip part of the operation pin 10 can be inserted into the hole 16 by inserting the operation pin 10 from the side part of the first coupling base 3. The hole 16 may be provided at only one place of two convex parts 15A and 15A of the rotor 12. When the operation cover 13 is located at the position oppositely oriented for handling, the hole 16 may be coincided with the hole 16 formed at the opposite hand position of the first coupling base 3 by rotating the rotor 12.

FIG. 3A and FIG. 3B show two embodiments of the rotors 12. The rotor 12 shown in FIG. 3A has a rib plate 21 formed at the bottom so as to improve the intensity. The recessed groove 5B for arraying and charging the spheres 8 is formed by the upper surface of the rib plate 21, the outer diameter part 20 and the outer circumferential wall of the recessed groove 5A is formed on the first coupling base 3. The recessed groove 5B for arraying and charging the spheres 8 is formed by the outer diameter part 20 and the outer circumferential wall of the recessed groove 5A is formed on the first coupling base 3 without providing the rib plate at the bottom so as to make the rotor 12 shown in FIG. 3B simple.

The recessed groove 5B is divided into two by the convex part 15A provided at two positions of the outer diameter part 20 of the rotor 12, and the spheres 8 are arrayed and charged. The spheres 8 are charged in the recessed groove 5B of one bisected half, and the freely expansible and contractible spring 15 is attached in the recessed groove 3B of the other half. Thereby, the joint coupling for the prosthetic brace capable of training the movable region of the joint and increasing muscle power can be obtained.

The diameter of the spheres 8 arrayed and charged in the recessed groove 5B is approximately 2 mm to 4 mm, and steel balls obtained by quenching the surface are mainly used. The freely expansible and contractible spring which is inserted into the recessed groove 5B is rolled in the shape of a coil, and the coil-like outer diameter is approximately 2 mm to 4 mm.

Figure 5:
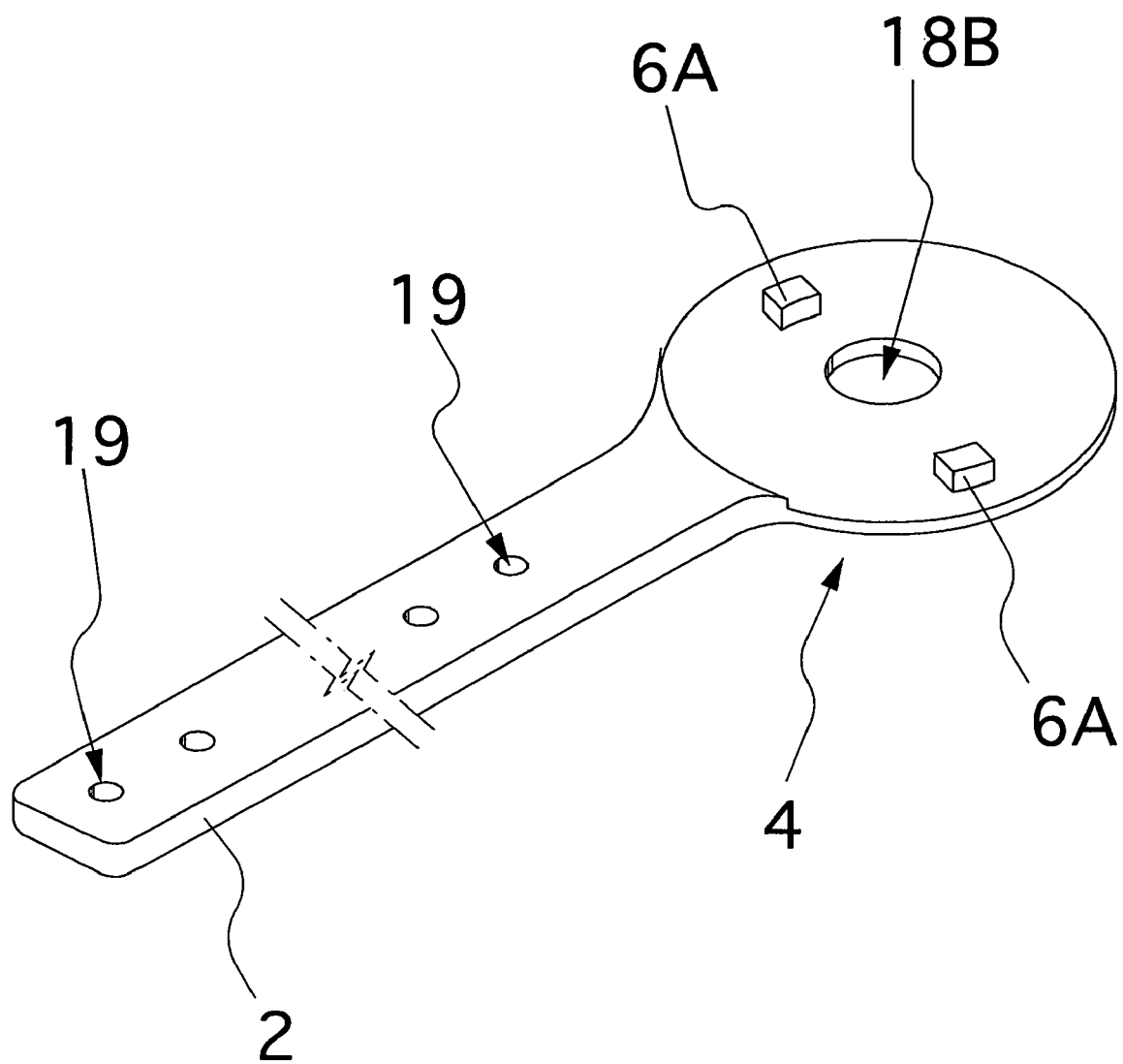
FIG. 5 is a perspective view of a lower coupling rod of a joint coupling for a prosthetic brace according to Example 2 of the present invention.

FIG. 5 is a perspective view of the lower coupling rod 2, and the disk-like second coupling base 4 is formed at the upper end. Protruding pieces 6A and 6A are provided on the outer peripheral surface of the second coupling base 4, and the protruding pieces 6A and 6A are fitted to the recessed groove 5B for arraying and charging the spheres 8. A bearing hole 18B for rotatably supporting the central shaft 7 is bored at the center of the second coupling base 4. The fitting holes 19 and 19 for attaching to the prosthetic brace are bored on the lower coupling rod 2.

One protruding piece 6A (right in Example 2) is brought into contact with one of the convex parts 15A and 15A provided at two positions of the outer diameter part 20 of the rotor 12 from its upper side. The other protruding piece 6A is brought into contact with the other convex part 15A from its lower side. One protruding piece 6A is brought into contact with the spheres 8 arrayed and charged by rotatably fitting into the recessed groove 5B for arraying and charging the spheres 8. In addition, the other protruding piece 6A is brought into contact with the one end of the freely expansible and contractible spring 15 attached to the other half of the recessed groove 5B, and is compressed by the rotation of the second coupling base 4. When muscle power is not increased, the spring 15 is not attached.

Figure 6:
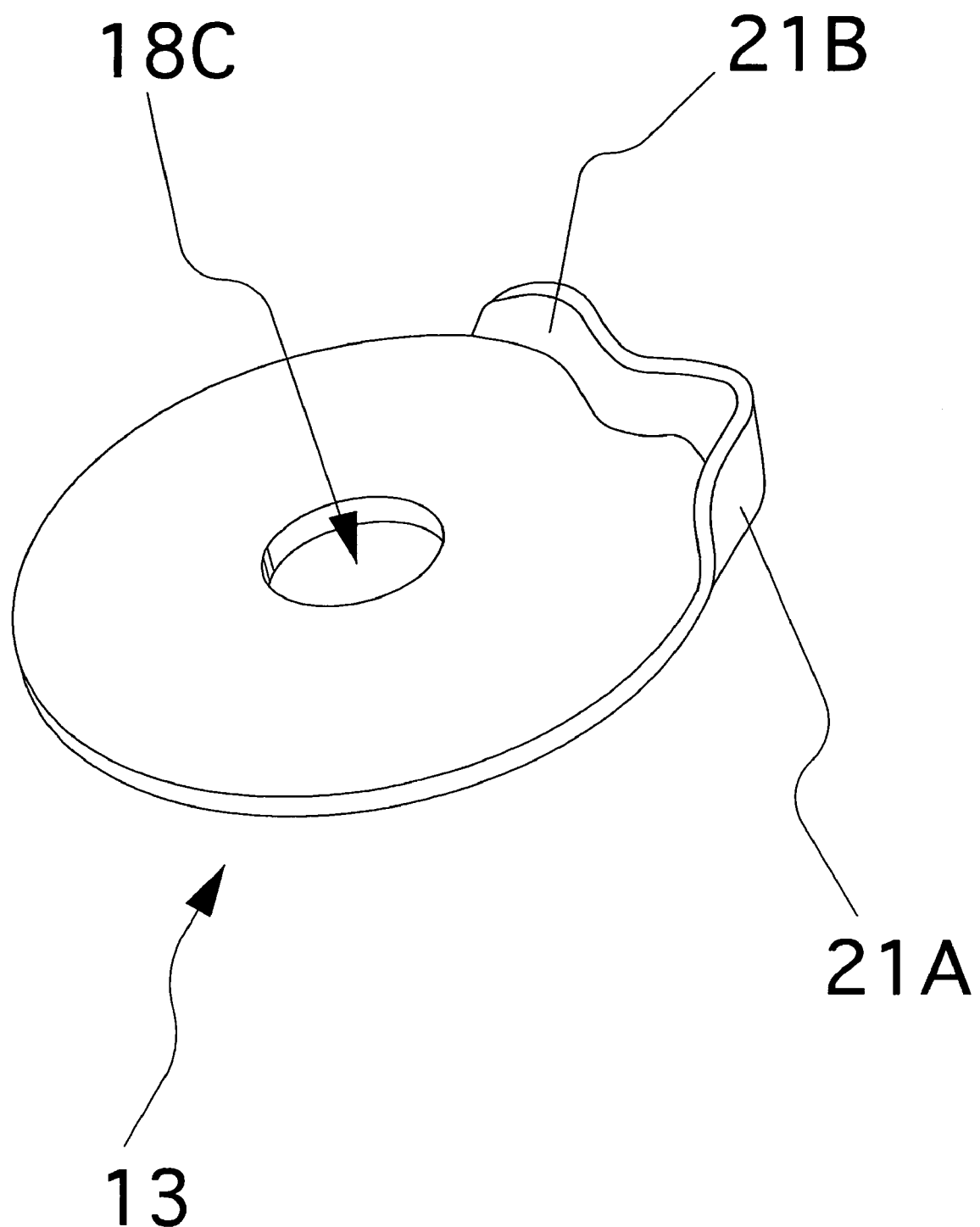
FIG. 6 is a perspective view of an operation cover of a joint coupling for a prosthetic brace according to Example 2 of the present invention.

FIG. 6 is a perspective view of the operation cover 13. So as to operate the operation pin 10, wavy recessed and projecting parts are formed on the disk-like circumference. A curved surface part 21A formed by enlarging the distance (size) from the center, and a curved surface part 21B formed by reducing the distance are provided. The tip part of the operation pin 10 is escaped from the hole 16 of the convex part 15A provided on the outer diameter part of the rotor 12 at the position where the head of the operation pin 10 is brought into contact with the curved surface part 21A, and the rotor 12 is freely rotated. The tip part of the operation pin 10 is inserted into the hole 16 of the convex part 15A at the position where the operation cover 13 is turned and the head of the operation pin 10 is brought into contact with the curved surface part 21B, and the rotor 12 is stopped. A bearing hole 18C for rotatably supporting the central shaft 7 is bored at the center of the operation cover 13.

The operation pin 10 has a circular head so as to be proficiently brought into contact with the circular surface of the curved surface parts 21A and 21B of the operation cover 13. The operation pin 10 is inserted via a coil spring 22 from the side part of the second coupling base 4 of the lower coupling rod 2. The head of the operation pin 10 is operated while being brought into contact with the surface of the wavy recessed and projecting parts by turning the operation cover 13, and is fitted at the positions of the curved surface parts 21A and 21B.

Next, the example of the using form will be explained in FIG. 7, FIG. 8 and FIG. 9.

Figure 7:
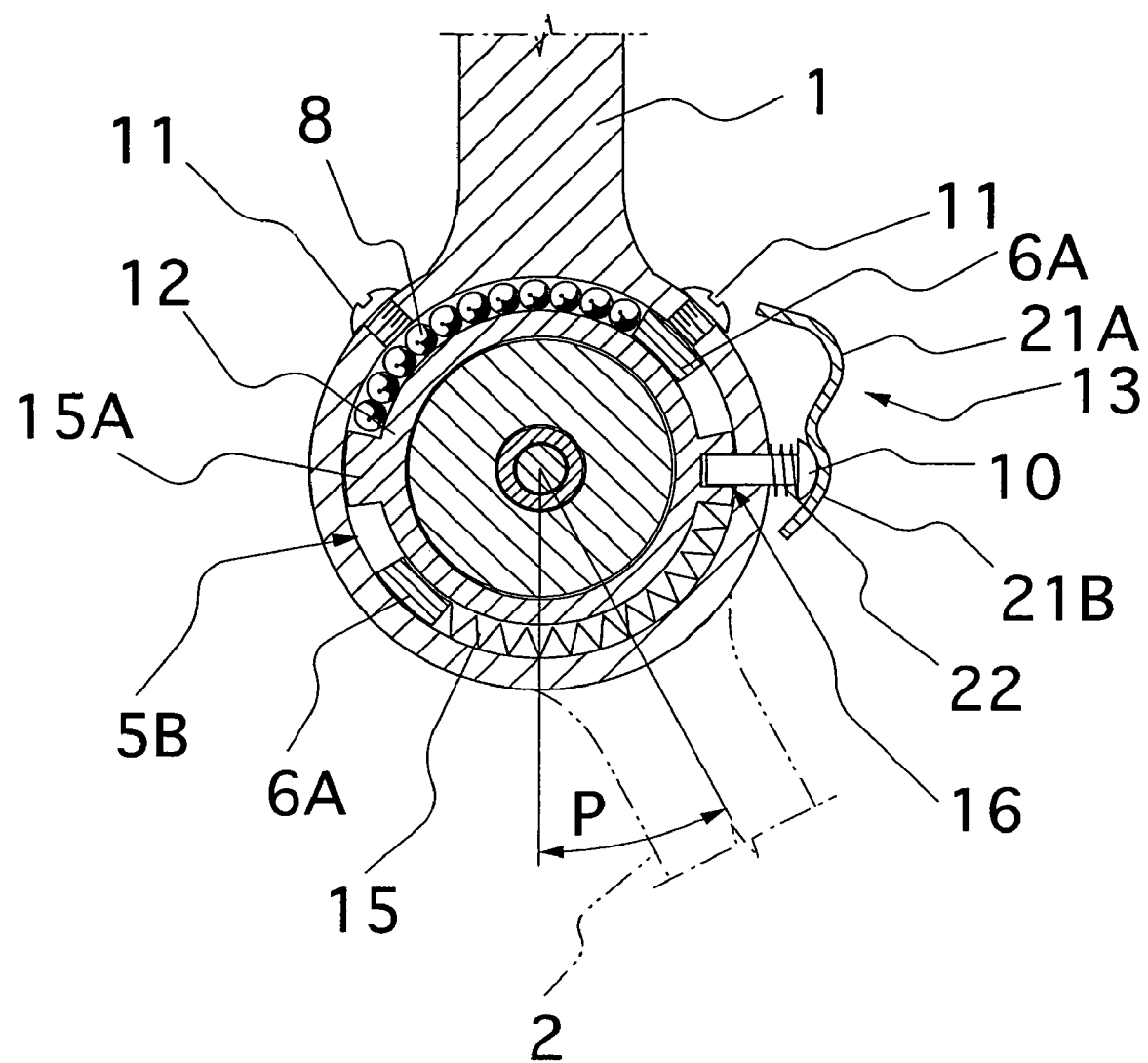
FIG. 7 is a plane sectional view of a using form adaptable for training in a movable region from a straight state of a joint coupling for a prosthetic brace according to Example 2 of the present invention.

FIG. 7 shows the using form in which the upper coupling rod 1 and the lower coupling rod 2 are adaptable for performing the movable training within the movable restriction region of a bending angle P from the straight state. The tip part of the operation pin 10 is pressed into the hole 16 of the convex part 15A provided on the outer diameter part at the position of the curved surface part 21B of the operation cover 13 from the side part of the first coupling base 3. The rotor 12 is stopped and fixed by the operation pin 10.

One (right) of the protruding pieces 6A and 6A provided on the second coupling base 4 of the lower coupling rod 2 is located at the upper part of the convex part 15A of one (right) of the convex parts 15A and 15A provided at two positions of the outer diameter part of the rotor 12 in the recessed groove 5B formed by the recessed groove 5A formed on the first coupling base 3, and the rotor 12 rotatably intruded into the recessed groove 5A. In addition, the other protruding piece 6A (left) is located and fitted at the lower part of the other (left) of the convex parts 15A and 15A. The upper coupling rod 1 and the lower coupling rod 2 are made into the straight state in the state where the rotor 12 is stopped by the operation pin 10 and the protruding pieces 6A and 6A are brought into contact with the convex parts 15A and 15A. The protruding piece 6A is caught between the spheres 8 and the convex part 15A by arraying and charging the spheres 8 in the recessed groove 5B with no gap, and the upper coupling rod 1 and the lower coupling rod 2 are fixed in the straight state. A gap S is generated by extracting the spheres 8, and the lower coupling rod 2 can be moved in the range of the bending angle P of the lower coupling rod 2 to the gap S. The protruding piece 6A provided on the second coupling base 4 hits the spheres 8, and thereby the movement of the lower coupling rod 2 is controlled.

The movable region training is performed by regulating within the range of the bending angle P of the lower coupling rod 2 to the above gap S. As the joint receiving damage is improved, the range of the movable region is expanded by extracting the spheres 8 to increase the gap S, and the bending angle P is enlarged, and the movable region training can be performed. The spheres 8 are taken in and out by removing the lid screw 11 screwed into the screw hole of the side part of the first coupling base 3 and blocking the screw hole. It is possible to walk in the range wherein the bending angle is 0° to 30°.

Since the end of the freely expansible and contractible spring 15 which is attached to the recessed groove 5B of the other half in which the spheres 8 bisected by the convex parts 15A and 15A provided at two positions of the outer diameter part of the rotor 12 are not attached is pushed and compressed by the protruding piece 6A provided on the second coupling base 4 of the lower coupling rod 2 according to the above movable region training, the spring force is added to the lower coupling rod 2, and muscle power can be increased. When the patient strains to move and cannot increase muscle power, the patient may remove the spring.

Figure 8:
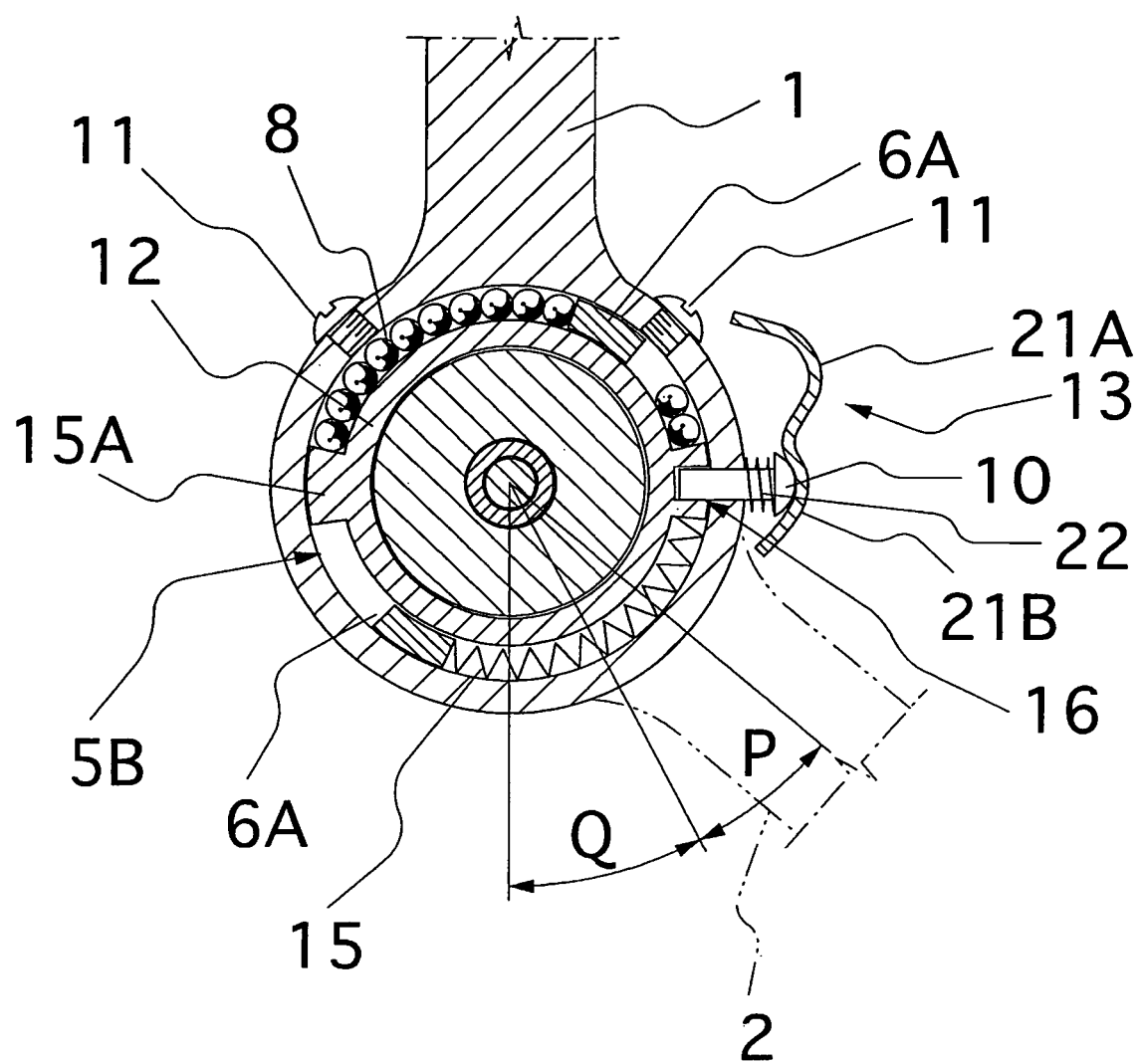
FIG. 8 is a plane sectional view of a using form adaptable for training in a movable region from bending jam.

FIG. 8 shows the using form in the case of performing the movable region training in the range of the bending angle P of the lower coupling rod 2 to the gap S from the state in which the lower coupling rod 2 is bent at the fixed angle Q. The angle Q is determined by inserting the spheres 8 between the protruding piece 6A provided on the second coupling base 4 of the lower coupling rod 2 and the convex parts 15A provided on the outer diameter part of the rotor 12. The angle deduced according to the distance (size) to the center of the sphere 8 can be calculated. When the lower coupling rod 2 is fixed at the angle Q, the angle Q is decided by interposing the spheres 8 between the convex part 15A provided on the outer diameter part of the rotor 12 and the protruding piece 6A provided on the second coupling base 4 of the lower coupling rod 2. The lower coupling rod 2 is caught and fixed between the spheres by arraying and charging the spheres 8 with no gap.

Figure 9:
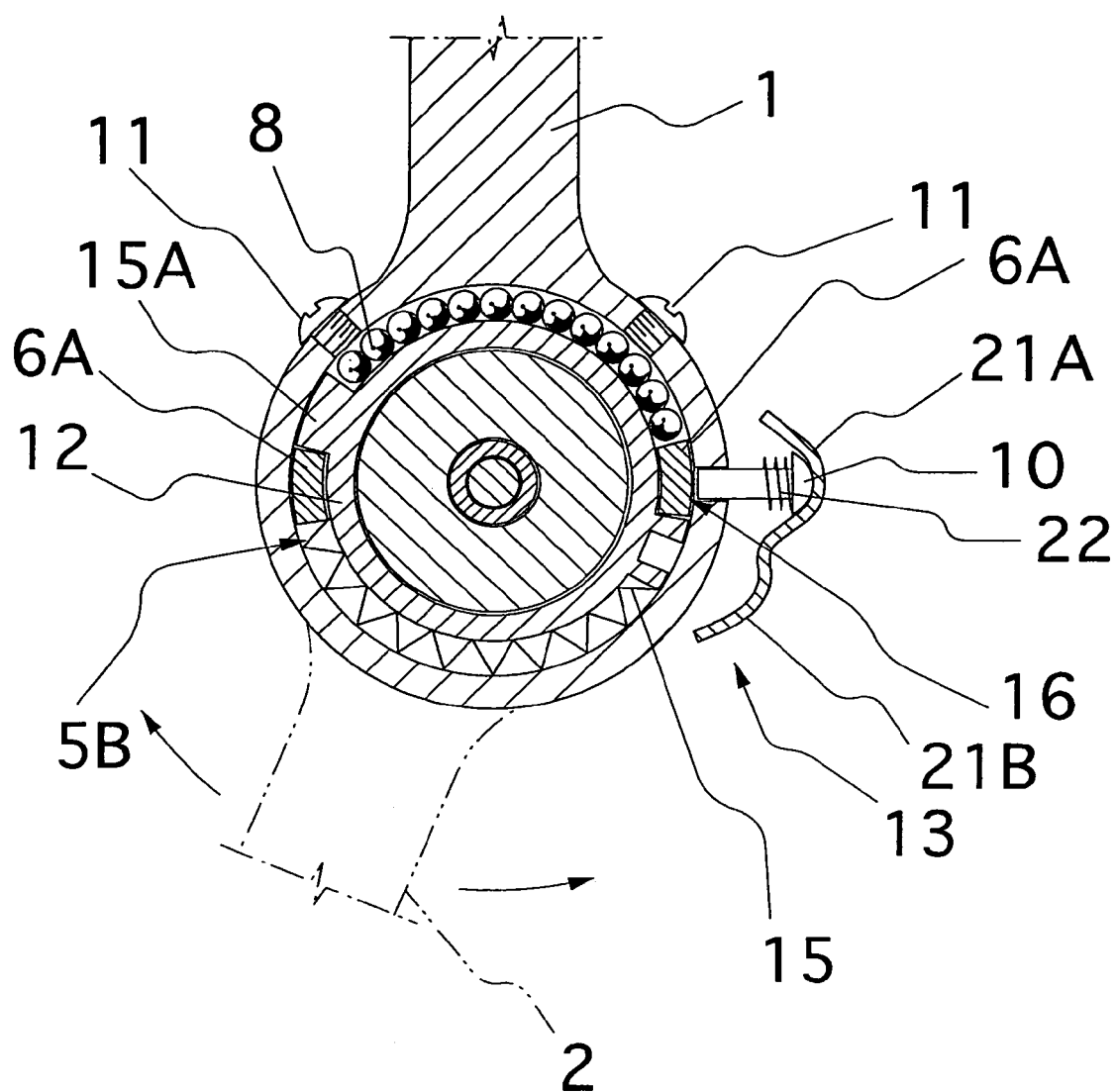
FIG. 9 is a plane sectional view of a rotatable state of a joint coupling for a prosthetic brace according to Example 2 of the present invention.

FIG. 9 shows the state where the head of the operation pin 10 is located at the curved surface part 21A of the operation cover 13 by operating the operation cover 13, the tip part of the operation pin 10 is escaped from the hole 16 formed on the convex part 15A of the rotor 12 by the coil spring 22, and the lower coupling rod 2 is freely rotated (freely bent). For example, the using form is adaptable when the joint of the leg part receiving the damage is improved to the state where the patient can sit straight. Since the tip part of the operation pin 10 is escaped from the hole 16 formed on the convex part 15A of rotor 12, and the rotor 12 can be freely rotated, the spheres 8 stopped by the convex part 15A of the rotor 12 can be freely rotated along the circumference of the recessed groove 5B, and the lower coupling rod 2 in which the protruding piece 6A is caught between the spheres 8 and the convex part 15A of the rotor 12 can be freely rotated.

Figure 11:
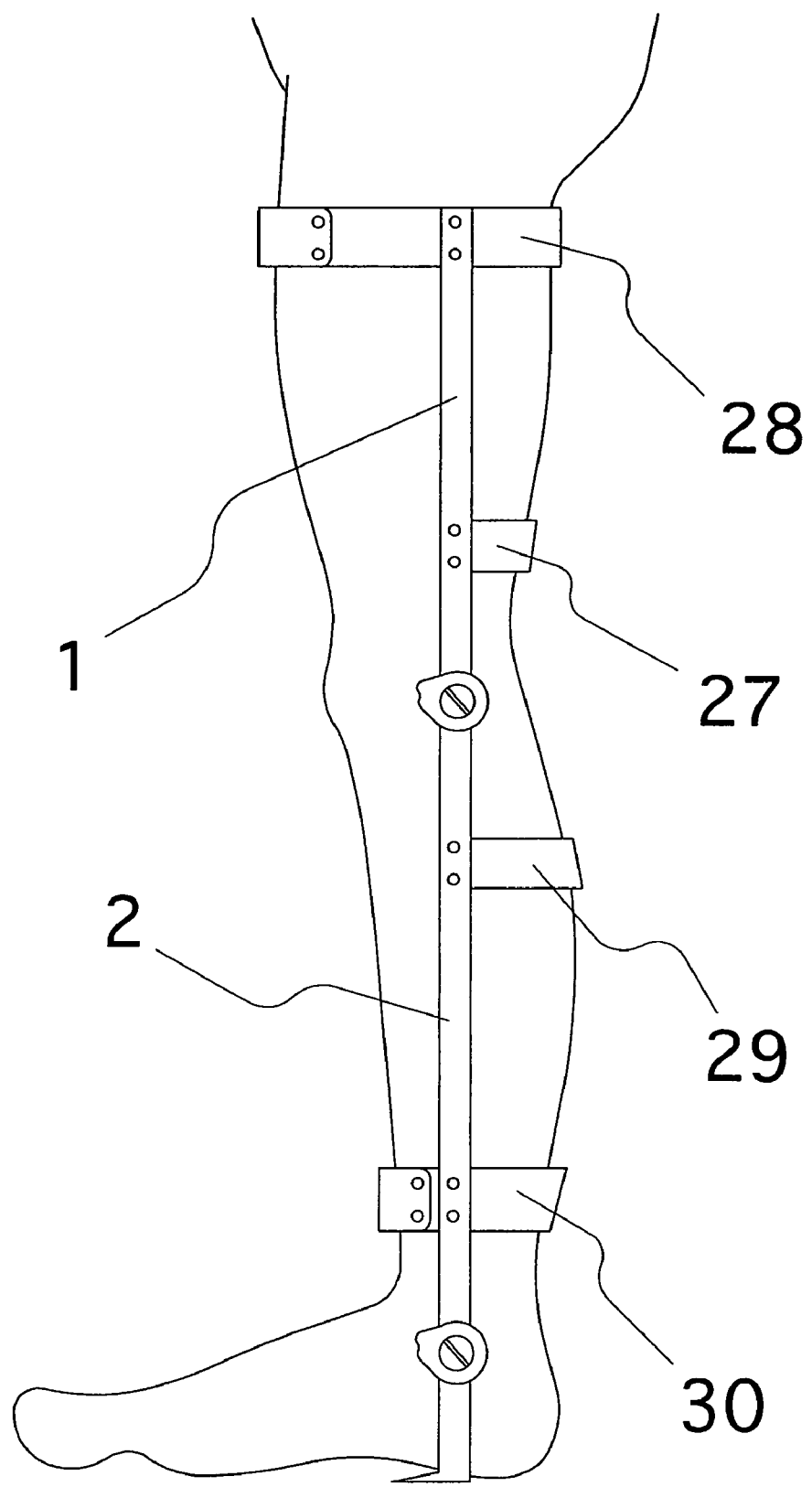
FIG. 11 is an explanatory view showing the state where a prosthetic brace to which the present invention is attached is attached to a leg part.

FIG. 10 and FIG. 11 show an example in which the prosthetic brace to which the joint coupling described above is attached is attached to an arm part and leg part of a body.

In the case of the arm part shown in FIG. 10, the upper coupling rod 1 is attached to an upper arm distant meniscus 23 and an upper arm proximal meniscus 24 with a cuffband, and is attached to an upper arm part. The lower coupling rod 2 is attached to a forearm proximal meniscus 25 and a forearm distant meniscus 26 with the cuffband, and is attached to a forearm part.

In the case of the leg part shown in FIG. 11, the upper coupling rod 1 is attached to a thigh distant meniscus 27 and a thigh proximal meniscus 28 with the cuffband, and is attached to a thigh part. The lower coupling rod 2 is attached to a lower thigh proximal meniscus 29 and a lower thigh distant meniscus 30 with the cuffband, and is attached to a lower thigh part.

EXAMPLE 3

Figure 13:
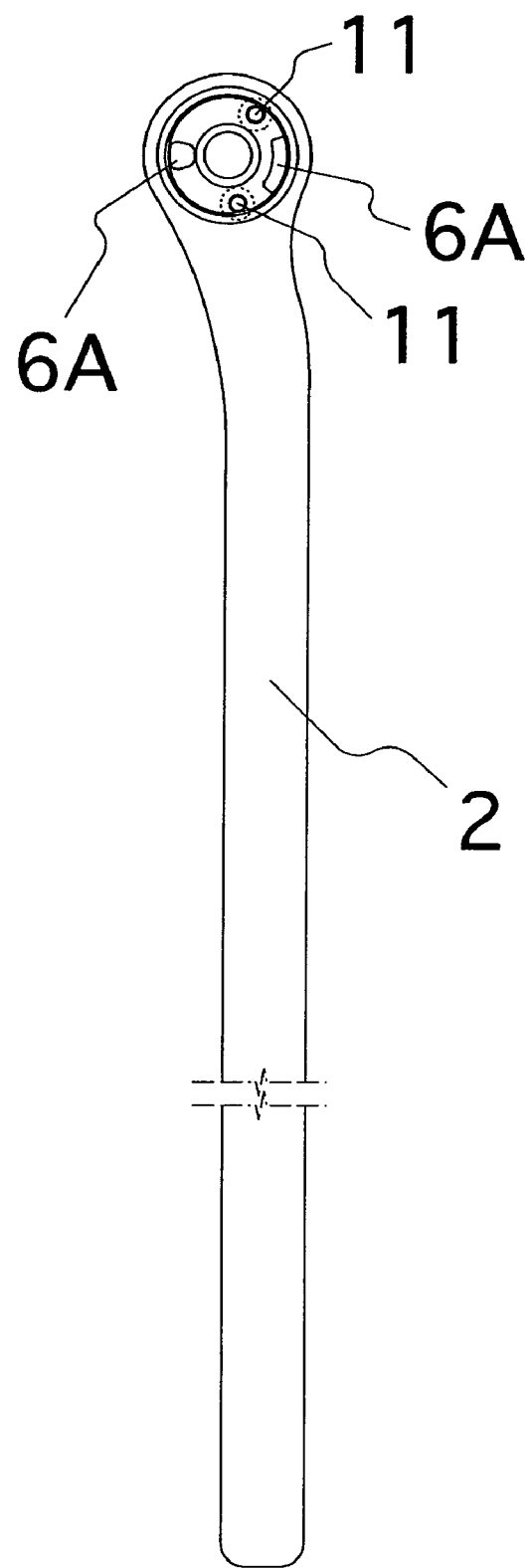
FIG. 13 is an explanatory view of a lower coupling rod of a joint coupling for a prosthetic brace according to Example 3 of the present invention.

FIG. 12, FIG. 13 and FIG. 14 show the other example of the application of the deterrence mechanism of the rotor due to the operation pin. As shown in Example 2, the disk-like first coupling base 3 and second coupling base 4 are formed at the lower end part of the upper coupling rod 1 and the upper end of the lower coupling rod 2. The rotor 12 is rotatably intruded into the first coupling base 3, and the recessed groove 5B for arraying and charging the spheres 8 is formed on the rotor 12.

The convex parts 15A and 15A are provided at two positions of the outer diameter part of the rotor 12, and the circumference of the recessed groove 5B for arraying and charging the spheres by the convex parts 15A and 15A is bisected. The spheres 8 are arrayed and charged in the recessed groove 5B of one bisected half, and a freely expansible and contractible spring 15 is attached to the recessed groove 5B of the other half. The operation pin 10 is taken in/out of the hole 16 formed on the convex part 15A of the outer diameter part of the rotor 12 from the side part of the first coupling base 3, and thereby the rotor 12 can be stopped or can be freely rotated.

The protruding pieces 6A and 6A are provided and fitted on the circumferential surface of the second coupling base 4 of the lower coupling rod 2. In addition, the second coupling base 4 is pivoted so as to be rotated to the first coupling base 3 by the central shaft 7 and the stopper screw 14 for preventing the fall off of the central shaft 7.

Then, as a mechanism for taking in/out the operation pin 10 the hole 16 formed on the convex part 15A of the outer diameter part of the rotor 12 from the side part of the first coupling base 3, a projection part 32 in which the through-hole 31 communicated with the insertion hole 17 for inserting the operation pin 10 from the side part on the side part of the first coupling base 3 is bored is formed. A pull type operation button 33 to which the operation pin 10 is connected via a compressed spring 34 is attached to the projection part 32.

Figure 15:
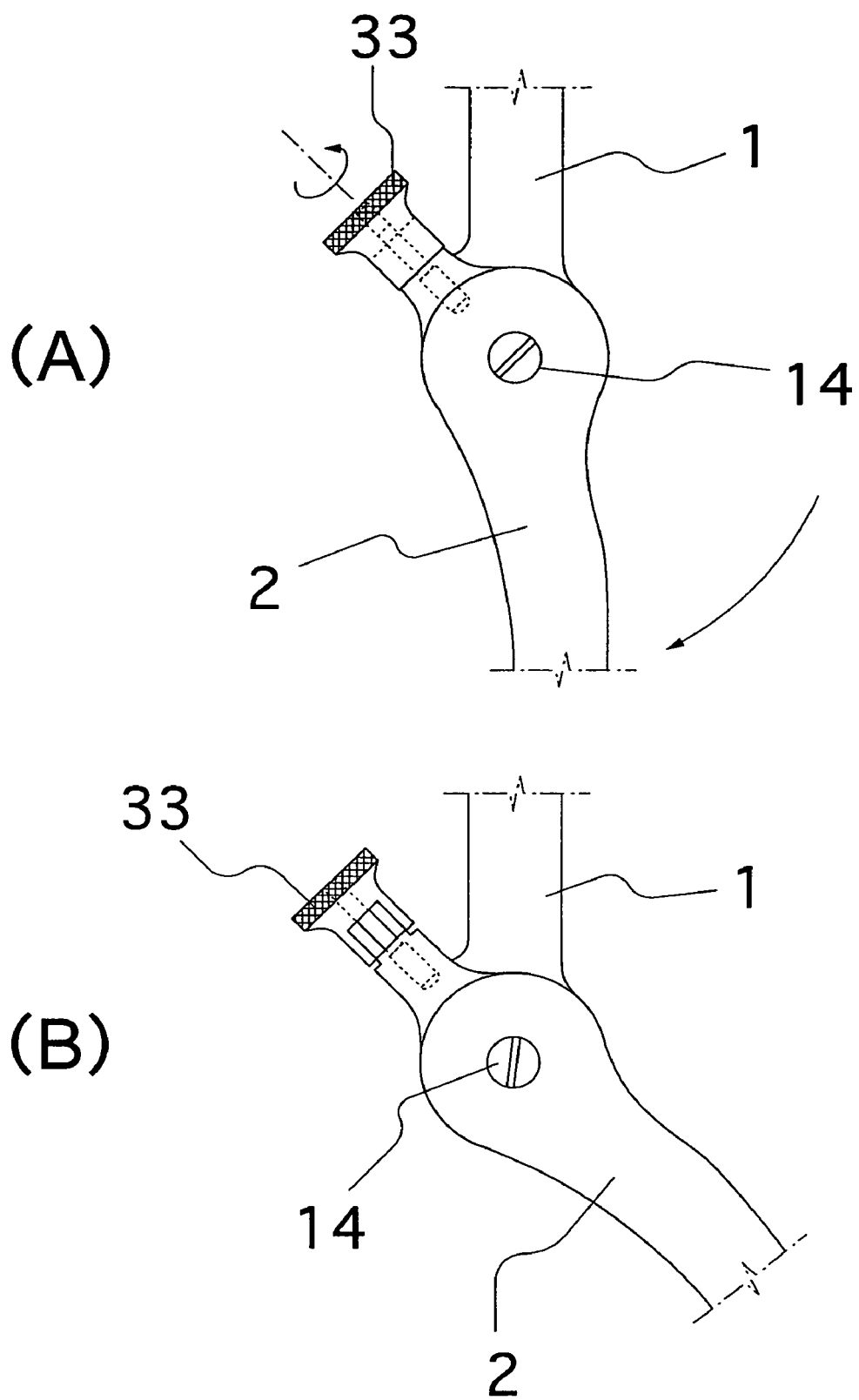
FIG. 15 is an explanatory view showing the action state of an operation pin of a joint coupling for a prosthetic brace according to Example 3 of the present invention.

Herein, as shown in FIG. 15A and FIG. 15B, during rehabilitation, the tip of the operation pin 10 is inserted into the hole 16 formed on the convex part 15A of the outer diameter part of the rotor 12 by the spring force of the compressed spring 34 provided in the through-hole 31, and the pull type operation button 33 is provided at the upper end of the projection part 32.

At the time of releasing the locking of the rotor, the lower end of the pull type operation button 33 is locked in the upper end of the projection part 32 by pulling the pull type operation button 33 and turning the button by 90°, while resisting the spring force of the compressed spring 34. The lower coupling rod 2 can be freely rotated by 360° by maintaining the state where the tip of the operation pin 10 is drawn out from the hole 16 formed on the convex part 15A of the outer diameter part of the rotor 12.

The tip of the operation pin 10 is pressed into contact with the outer diameter part of the rotor 12 according to the spring force of the compressed spring 34 by pulling, turning by 90° and detaching the pull type operation button 33 at the time of locking the rotation of the rotor 12 again. The operation pin 10 goes around the outer diameter part of the rotor 12 by rotating the second coupling base 4 of the lower coupling rod 2 from this state. When the operation pin 10 coincides with the position of the hole 16 formed on the convex part 15A of the outer diameter part of the rotor 12, the tip of the operation pin 10 goes into the hole 16, and thereby the rotor 12 is locked. Thus, the rotor is locked and released by pulling and turning the pull type operation button 33, and the pull type operation button 33 can be easily operated by the patient himself.

Two screw holes having a diameter capable of freely taking in and out the spheres 8 are bored on the outer surface of the second coupling base 4 so that two screw holes are communicated with the recessed groove 5. Lid screws 11 for blocking the screw holes are screwed.

EXAMPLE 4

Figure 16:
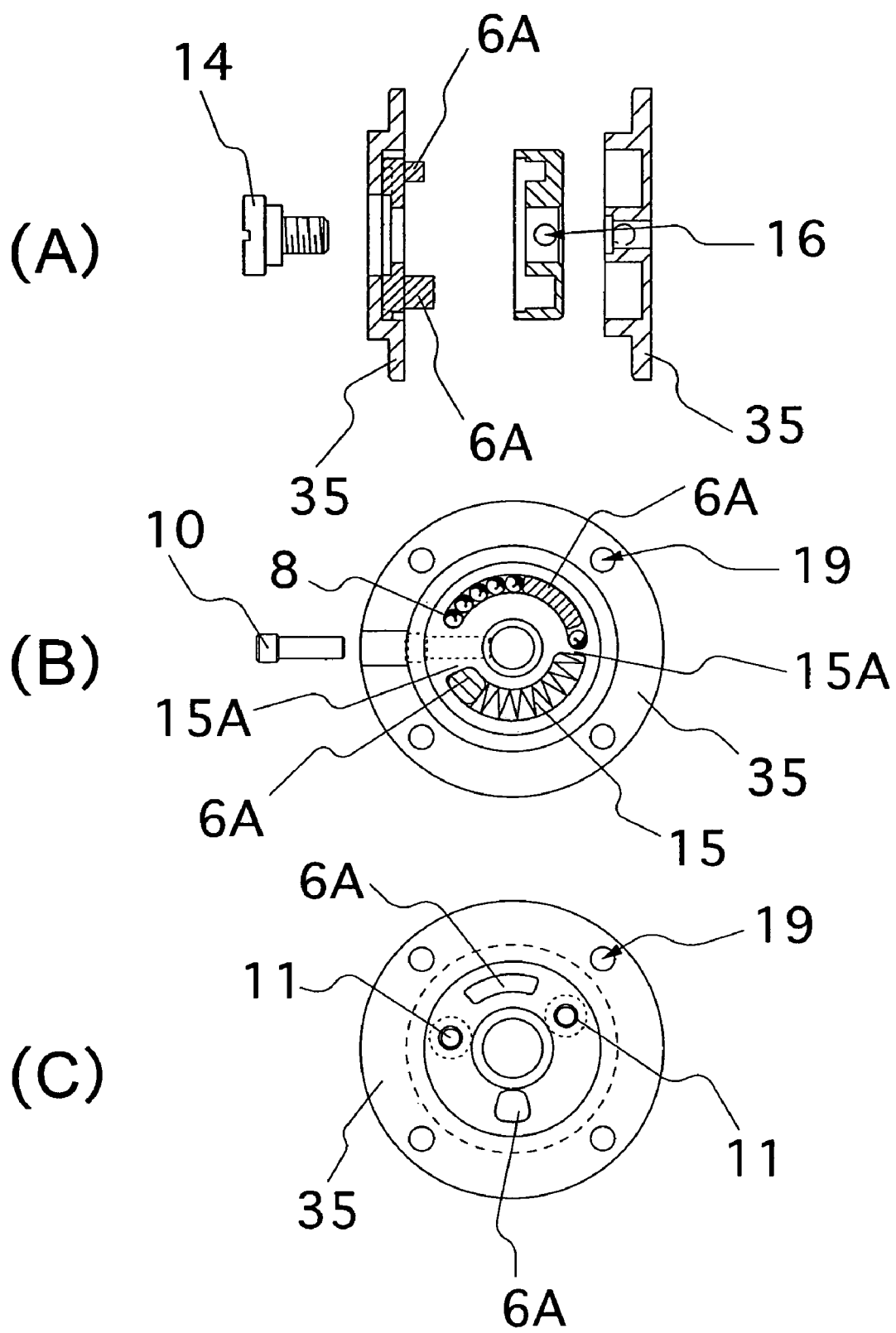
FIG. 16 is an explanatory view of a joint coupling for a prosthetic brace according to Example 4 of the present invention.

FIG. 16A, FIG. 16B and FIG. 16C show the example of application of the joint coupling for the prosthetic brace in the case of being used for the joint of the brace manufactured with plastic or the like based on the impression for a thigh, a lower thigh, an upper arm and a forearm or the like.

A fitting hole 19 is bored on a mounting flange 35 bulging out along the circumference of the first coupling base 3 and second coupling base 4. The rotor 12 is rotatably intruded into the first coupling base 3, and the recessed groove 5B for arraying and charging the spheres 8 is formed on the rotor 12.

The convex parts 1SA and 1SA are provided at two positions of the outer diameter part of the rotor 12, and the circumference of the recessed groove 5B for arraying and charging the spheres is bisected by the convex parts 15A and 15A. The spheres 8 are arrayed and charged in the recessed groove 5B of one bisected half, and a freely expansible and contractible spring 15 is attached to the recessed groove 5B of the other half. The operation pin 10 is taken in/out of the hole 16 formed on the convex part 15A of the outer diameter part of the rotor 12 from the side part of the first coupling base 3, and thereby the rotor 12 can be stopped or can be freely rotated.

Herein, a male screw is circumferentially formed on the outer peripheral surface of the operation pin 10, and a female screw is also installed in the insertion hole 17 bored on the side part of the first coupling base 3. The operation pin 10 is screwed into the insertion hole 17, and is taken in/out of the hole 16 formed on the convex part 15A of the outer diameter part of the rotor 12 by screwing the operation pin 10 by using an Allen wrench or the like.

Two screw holes having a diameter capable of freely taking in and out the spheres 8 is bored on the outer surface of the second coupling base 4 so that two screw holes are communicated with the recessed groove 5. The lid screw 11 for blocking the screw hole is screwed.

EXAMPLE 5

Figure 17:
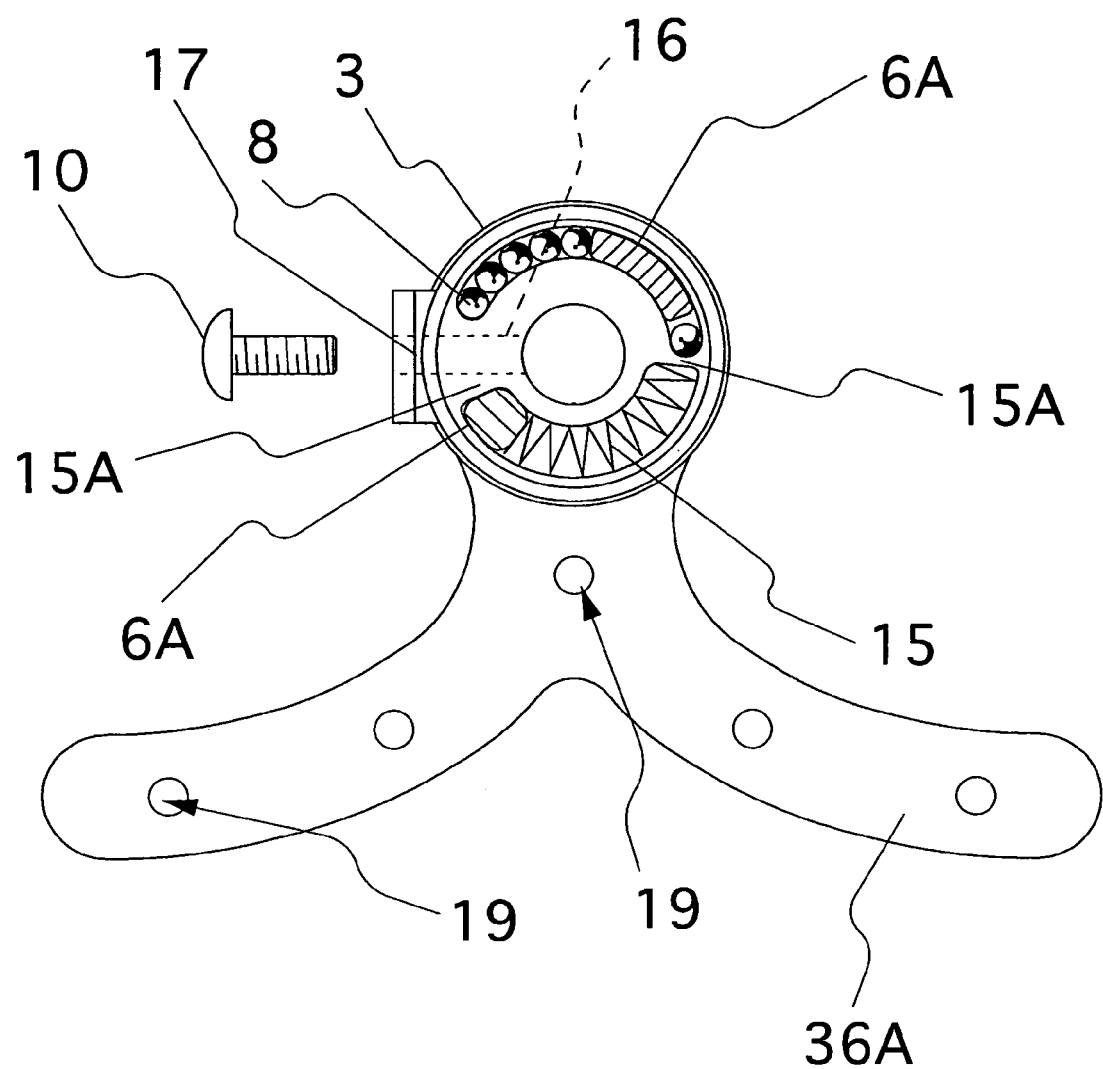
FIG. 17 is an explanatory view of a first coupling base of a joint coupling for a prosthetic brace according to Example 5 of the present invention.
Figure 18:
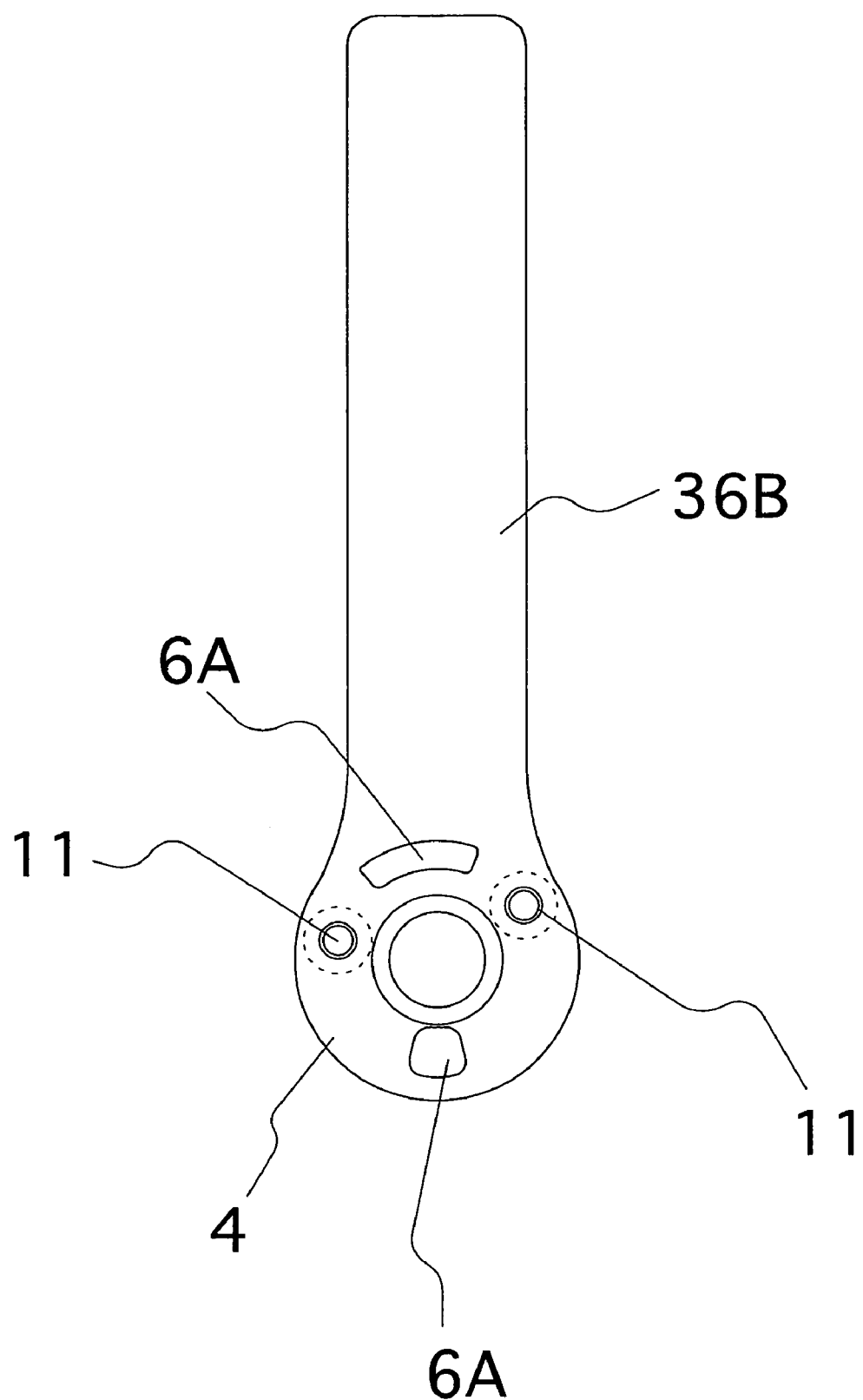
FIG. 18 is an explanatory view of a second coupling base of a joint coupling for a prosthetic brace according to Example 5 of the present invention.

FIG. 17, FIG. 18 and FIG. 19 show the example of the application of the joint coupling for the prosthetic brace in the case of being used for the joint of an ankle.

A fork-like coupling rod 36A for connecting to the brace attached to the foot part is formed at the lower part of the first coupling base 3, and a coupling rod 36B for connecting to the brace attached to the lower thigh is formed at the upper part of the second coupling base 4. The fitting holes 19 are further bored on the coupling rods 36A and 36B. The rotor 12 is rotatably intruded into the first coupling base 3, and the recessed groove 5B for arraying and charging the spheres 8 is formed on the rotor 12.

The convex parts 15A and 15A are provided at two positions of the outer diameter part of the rotor 12, and the circumference of the recessed groove 5B for arraying and charging the spheres is bisected by the convex parts 15A and 15A. The spheres 8 are arrayed and charged in the recessed groove 5B of one bisected half, and the freely expansible and contractible spring 15 is attached to the recessed groove 5B of the other half. The operation pin 10 is taken in/out of the hole 16 formed on the convex part 15A of the outer diameter part of the rotor 12 from the side part of the first coupling base 3, and thereby the rotor 12 can be stopped or can be freely rotated.

Herein, a male screw is circumferentially formed on the outer peripheral surface of the operation pin 10, and a female screw is also installed in the insertion hole 17 bored on the side part of the first coupling base 3. The operation pin 10 is screwed into the insertion hole 17, and is taken in/out of the hole 16 formed on the convex part 15A of the outer diameter part of the rotor 12 by screwing the operation pin 10 by using a driver or the like.

Two screw holes having a diameter capable of freely taking in and out the spheres 8 are bored on the outer surface of the second coupling base 4 so that two screw holes are communicated with the recessed groove 5. Lid screws 11 for blocking the screw holes are screwed.

Figure 21:
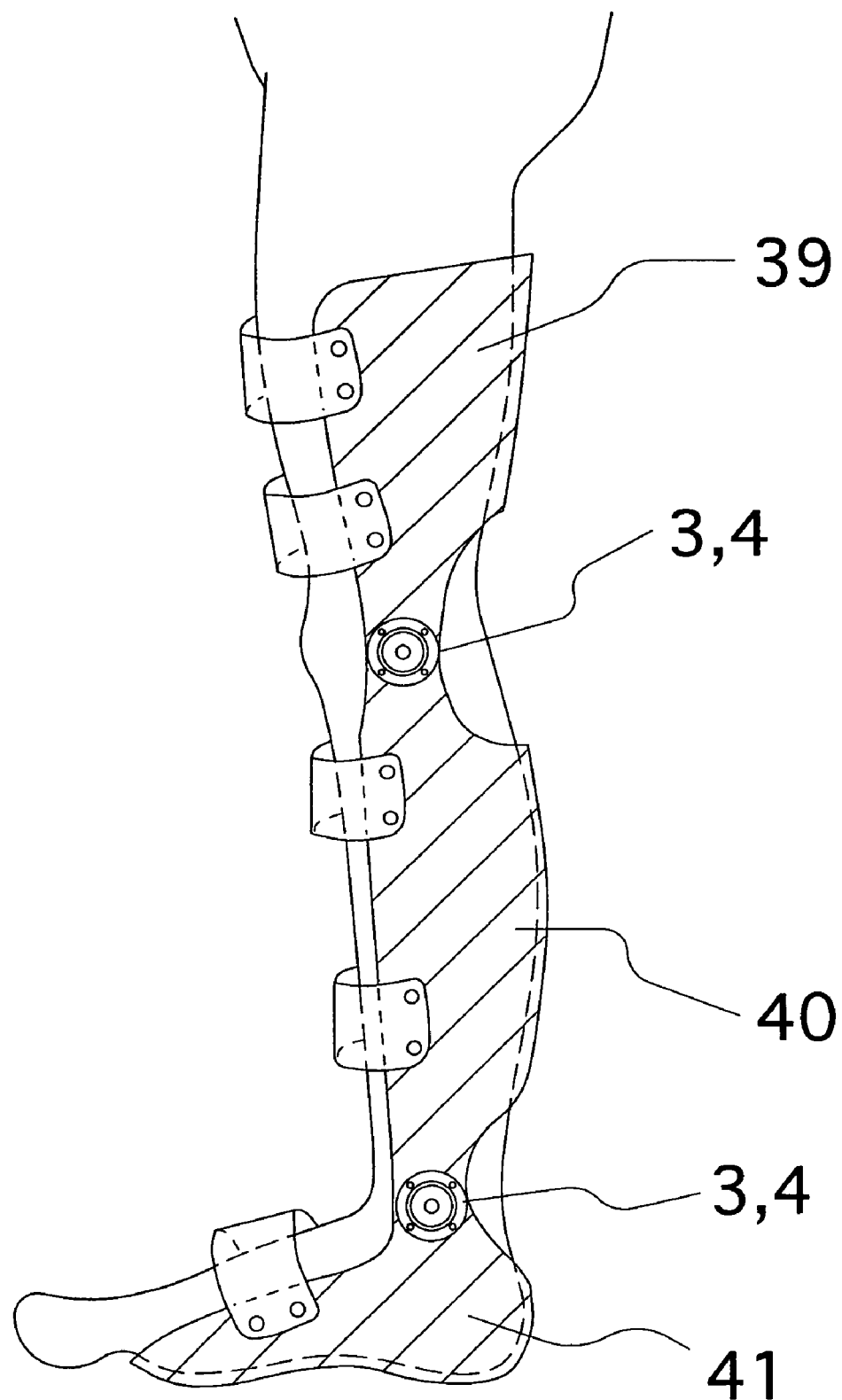
FIG. 21 is an explanatory view showing the state where a joint coupling for a prosthetic brace according to Example 4 of the present invention is attached to a thigh brace, a lower thigh brace and a foot brace.
Figure 22:
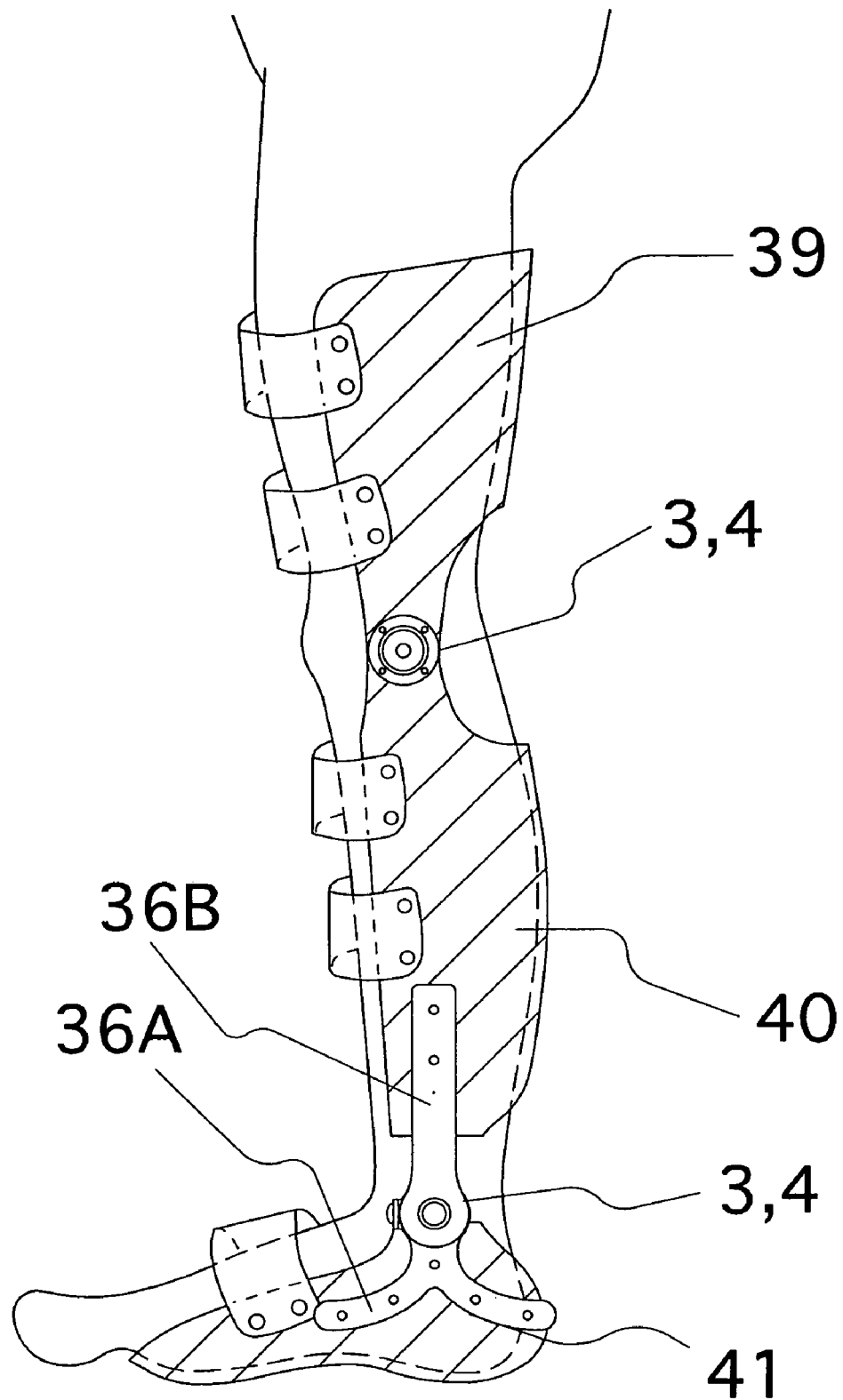
FIG. 22 is an explanatory view showing the state where a joint coupling for a prosthetic brace according to Example 5 of the present invention is attached to a lower thigh brace and a foot brace.

FIG. 20 and FIG. 21 show the example in which the prosthetic brace provided with the joint coupling explained in detail in Example 4 is attached to the arm part and leg part of the body.

As shown in FIG. 20, at the time of producing an elbow brace, a patient's upper arm and forearm are molded with gypsum. An upper arm brace 37 and forearm brace 38 with a cuffband molded with a plastic material based on the molding are produced. The first coupling base 3 and second coupling base 4 of the present invention are baked to fix to the upper arm brace 37 and the forearm brace 38 as the joint coupling of the upper arm brace 37 and forearm brace 38.

As shown in FIG. 21, when a knee brace is produced, a thigh brace 39 and lower thigh brace 40 with a cuffband molded with a plastic material are produced. The first coupling base 3 and second coupling base 4 of the present invention are baked to fix to the thigh brace 39 and the lower thigh brace 40 as the joint coupling of the thigh braces 39 and lower thigh brace 40. When an ankled-foot brace is produced, the first coupling base 3 and second coupling base 4 of the present invention are respectively baked to fix as the joint coupling of the lower thigh brace 40 and foot brace 41.

A brace obtained by respectively baking to fix the first coupling base 3 and second coupling base 4 of the present invention as the joint coupling of the thigh brace 39, the lower thigh brace 40 and the foot brace 41 is referred to as a knee ankled-foot brace.

The mechanism explained in detail in Example 5 may not be necessarily used as the mechanism for locking or releasing the rotor by using the operation pin, and any mechanism may be used as long as the mechanism can lock or release the rotor easily.

EXAMPLE 6

Figure 23:
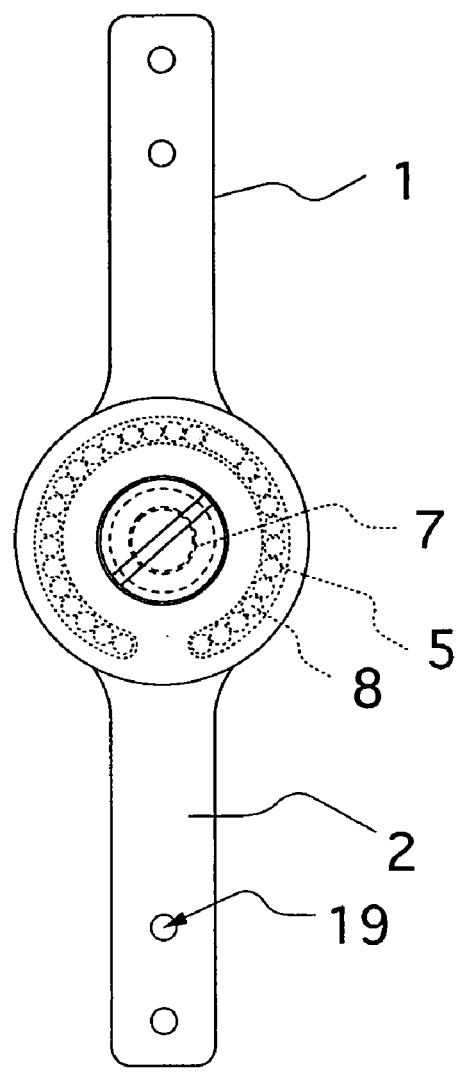
FIG. 23 is an explanatory view of a joint coupling for a prosthetic brace according to Example 6 of the present invention.
Figure 23:
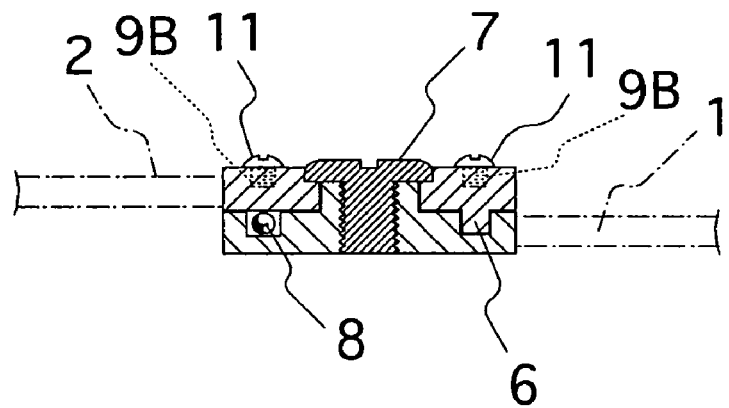

As shown in FIG. 23A and FIG. 23B, the disk-like first coupling base 3 and the second coupling base 4 are provided at the lower end part of the upper coupling rod 1 and the upper end part of the lower coupling rod 2. The recessed groove 5 is formed along the circumference of the first coupling base 3.

The protruding piece 6 fitted to the recessed groove 5 is formed on the circumferential surface of the second coupling base 4, and the first coupling base 3 and the second coupling base 4 are mutually pivoted in a rotatable state by the central shaft 7.

A plurality of spheres 8 formed of a superhard steel material are charged in the recessed groove 5 formed along the circumference of the first coupling base 3 in the state where the protruding piece 6 of the second coupling base 4 is sandwiched. In addition, two screw holes 9B having the diameter for freely taking in and out the spheres 8 are bored on the outer surface of the second coupling base 4 so that the screw holes 9B are communicated with the recessed groove 5. The lid screw 11 for blocking the screw hole 9B is screwed into the screw hole 9B.

Herein, for example, the upper coupling rod 1 as a fixation side and the lower coupling rod 2 as a movable side are attached to a prosthesis or a brace. When the spheres 8 are charged in the state where a gap is not generated in the recessed groove 5, the rotation movement of the spheres 8 in the recessed groove 5 is stopped, and the rotation of the second coupling base 4 is locked. Next, a gap is generated between the spheres 8 by removing the lid screw 11 from this state and extracting the required number of spheres 8 charged in the recessed groove 5. The spheres 8 are rotated and moved by the length of the gap, and the protruding piece 6 of the second coupling base 4 can be moved in the recessed groove 5. Therefore, the movable region of the second coupling base 4 can be set by taking in and out the spheres 8.

EXAMPLE 7

As shown in FIG. 24A and FIG. 24B, the disk-like first coupling base 3 and the second coupling base 4 are provided at the lower end part of the upper coupling rod 1 and the upper end part of the lower coupling rod 2. The recessed grooves 5A and 5A substantially half-split to the left and right are formed along the circumference of the first coupling base 3.

The protruding pieces 6A and 6A are formed on the circumferential surface of the second coupling base 4 of the lower coupling rod 2. The protruding pieces 6A and 6A are fitted to the recessed grooves 5A and SA of the first coupling base 3, and the first coupling base 3 and the second coupling base 4 are mutually pivoted in a rotatable state by the central shaft 7.

Thereby, the spheres 8 are arrayed and charged in one half of the recessed grooves 5A and 5A substantially half-split to the left and right along the circumference of the first coupling base 3. The freely expansible and contractible spring 15 is attached to the recessed groove 5A of the other half. One of the protruding pieces 6A and 6A provided on the second coupling base 4 is caught by pressing down using the sphere 8, and is fixed in the straight state. The lower coupling rod 2 can be rotated within the range of the gap of the extracted spheres by extracting the spheres 8. The other protruding piece 6A provided on the second coupling base 4 of the lower coupling rod 2 by the rotation of the lower coupling rod 2 pushes the freely expansible and contractible spring 15, and the force of the spring is applied to the protruding piece 6A.

Figure 25:
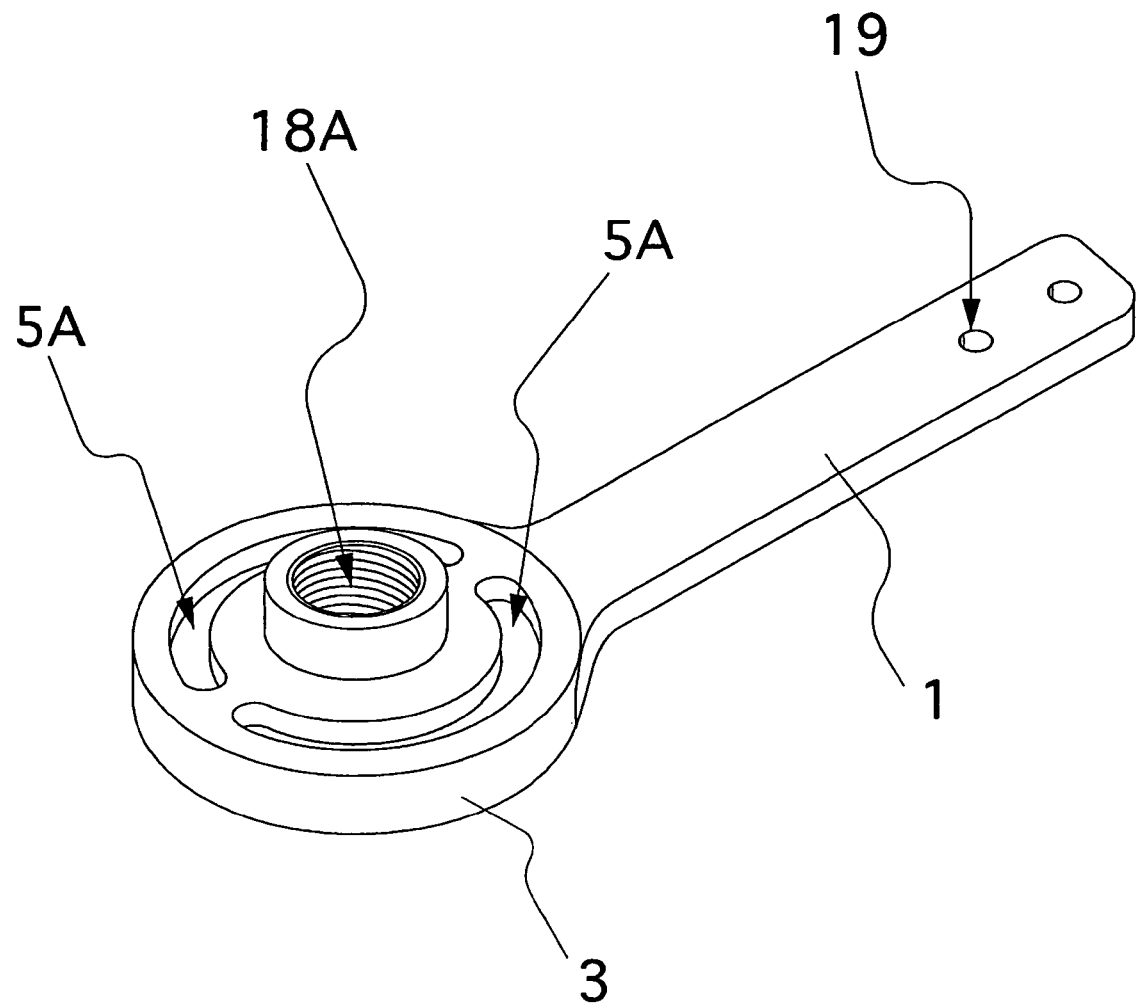
FIG. 25 is an explanatory view of a first coupling base of a joint coupling for a prosthetic brace according to Example 7 of the present invention.

FIG. 25 is a perspective view of the upper coupling rod 1, and the first coupling base 3 is formed at the lower end part. The recessed grooves 5A and 5A are formed along the circumference of the first coupling base 3. The recessed grooves 5A and SA are substantially half-split in a circular shape to the left and right, and the bearing hole 18A for rotatably supporting the central shaft is bored at the center of the first coupling base 3. The fitting holes 19 and 19 for attaching to the prosthetic brace are bored on the upper coupling rod 1.

Figure 26:
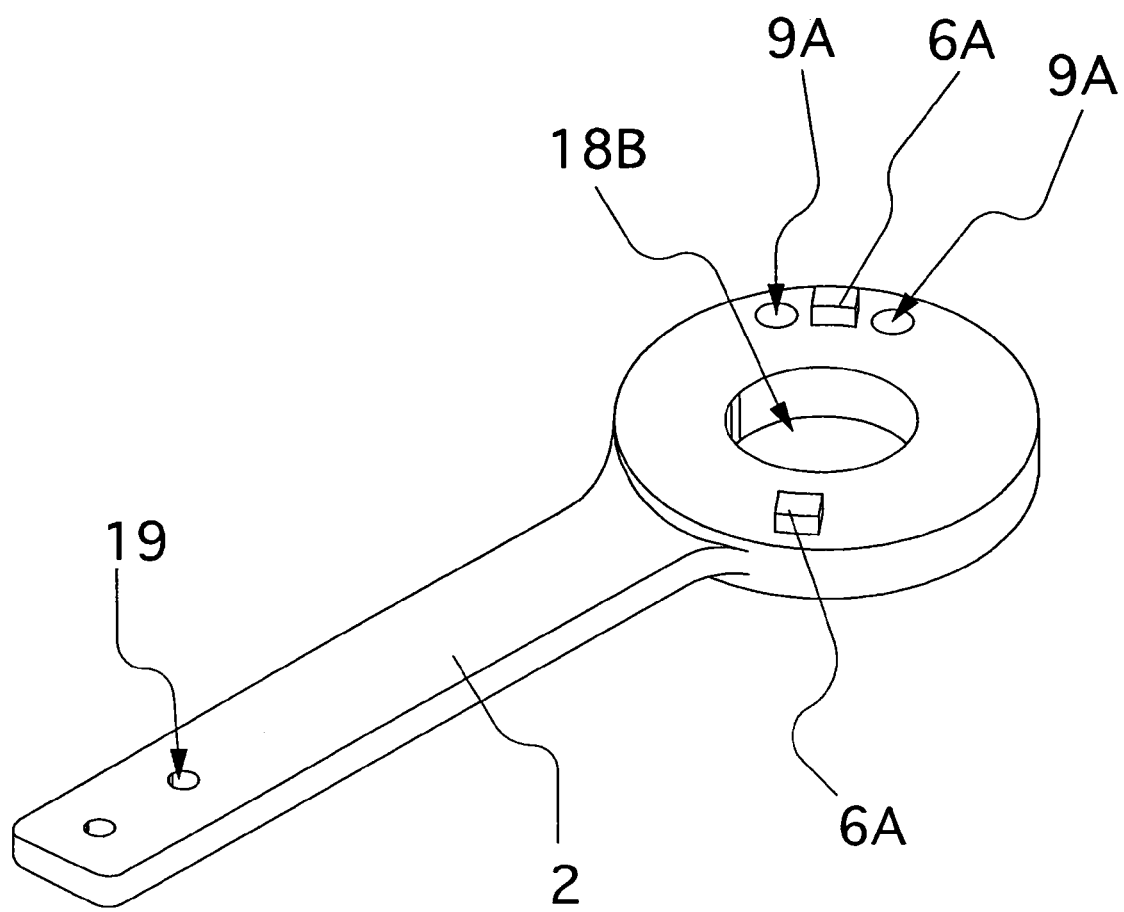
FIG. 26 is an explanatory view of a second coupling base of a joint coupling for a prosthetic brace according to Example 7 of the present invention.

FIG. 26 is a perspective view of the lower coupling rod 2, and the second coupling base 4 is formed at the upper end thereof. Two protruding pieces 6A and 6A are protruded on the circumferential surface of the second coupling base 4 so as to be fitted to the recessed grooves 5A and 5A formed on the first coupling base 3. The screw holes 9A and 9A for taking in and out the spheres of the recessed groove 5A of the first coupling base 3 are screwed by the lid screw 11 at one of two protruding pieces 6A and 6A. The bearing hole 18B for rotatably fitting to the bearing hole 18A protruded at the central part of the first coupling base 3 is bored at the center of the second coupling base 4.

Next, the using form of the movable region training due to the joint coupling for the prosthetic brace in Example 7 is explained in FIG. 27A and FIG. 27B.

FIG. 27A shows the example of the using form adaptable for performing the movable training within the movable region of the bending angle P of the range of the gap S obtained by extracting the spheres 8 arrayed and charged in the recessed groove 5A of one half from the straight state of the lower coupling rod 2 to the upper coupling rod 1. The rotation of the lower coupling rod 2 is regulated by hitting the protruding piece 6A against the spheres 8 within the range of the gap S. The freely expansible and contractible spring 15 attached to the recessed groove 5A of the other half is pushed by the other protruding piece 6A, and the force of the spring is applied to the lower coupling rod 2.

FIG. 27B shows the example of the using form adaptable for performing the movable training within the movable region of the bending angle P of the range of the gap S obtained by extracting the spheres 8 arrayed and charged in the recessed groove 5A of one half from the state of the bending angle Q of the lower coupling rod 2 to the upper coupling rod 1. The rotation of the lower coupling rod 2 is regulated by hitting the protruding piece 6A against the spheres within the range of the gap S. The freely expansible and contractible spring 15 attached to the recessed groove 5A of the other half is pushed by the other protruding piece 6A, and the force of the spring is applied to the lower coupling rod 2.

When the spheres 8 having the gap S are packed, the protruding piece 6A is caught by the spheres 8, and the lower coupling rod 2 is fixed in the state of the bending angle P+Q.

EXAMPLE 8

Figure 28:
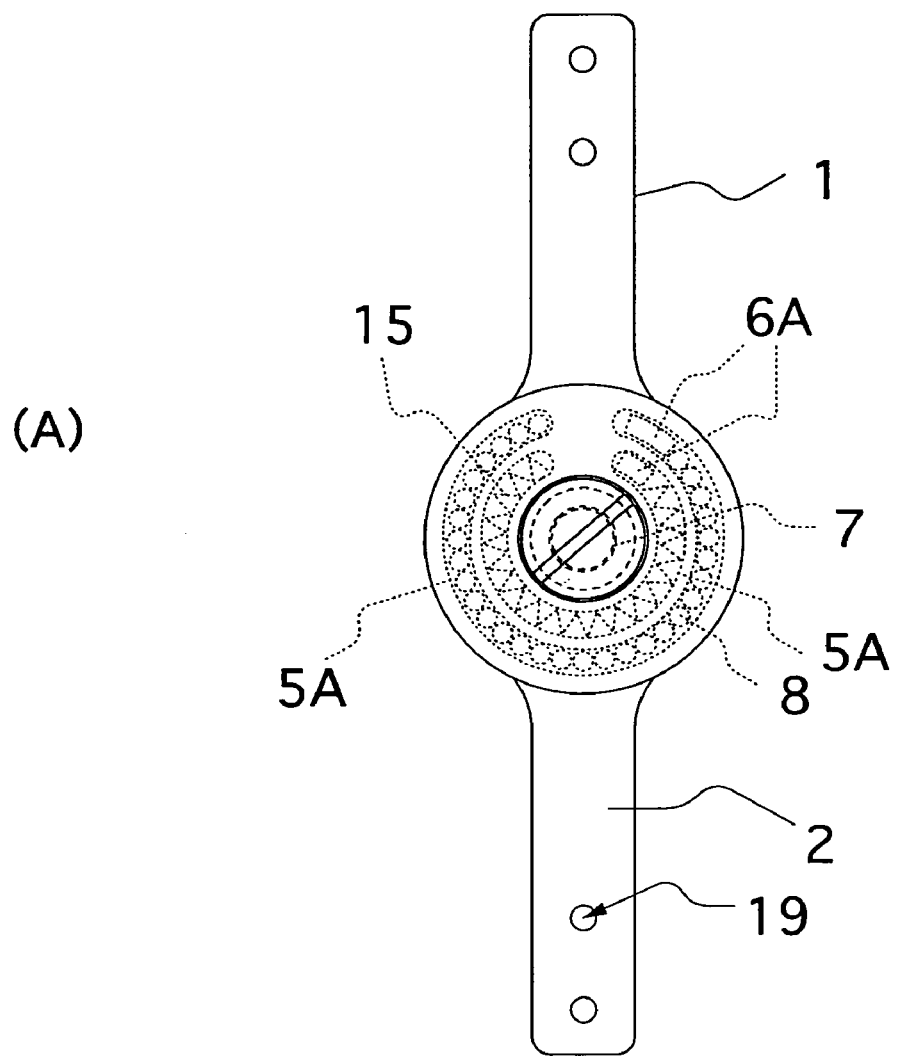
FIG. 28 is an explanatory view of a joint coupling for a prosthetic brace according to Example 8 of the present invention.
Figure 28:
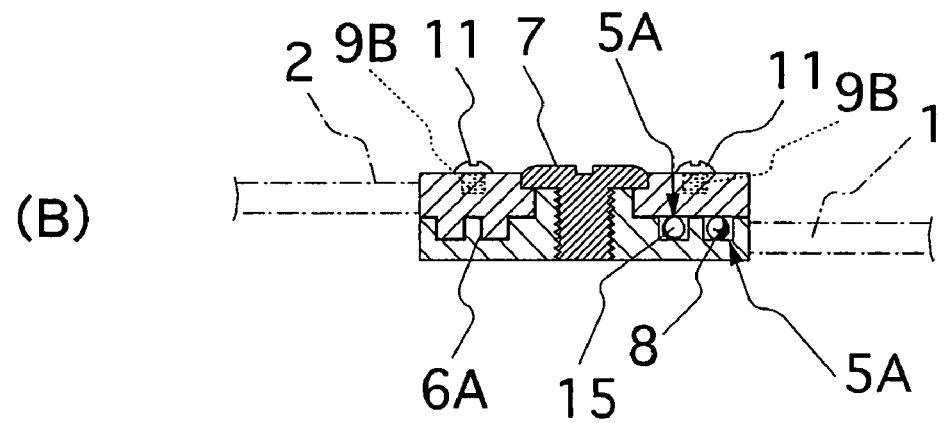

As shown in FIG. 28A and FIG. 28B, the disk-like first coupling base 3 and the second coupling base 4 are provided at the lower end part of the upper coupling rod 1 and the upper end part of the lower coupling rod 2. Two-row recessed grooves 5A and 5A are formed along the circumference of the first coupling base 3.

The protruding pieces 6A and 6A are formed on the circumferential surface of the second coupling base 4 of the lower coupling rod 2. The protruding pieces 6A and 6A are fitted to the recessed grooves 5A and 5A of the first coupling base 3, and the first coupling base 3 and the second coupling base 4 are mutually pivoted in a rotatable state by the central shaft 7.

The spheres 8 are arrayed and charged in the recessed groove 5A of the first row of two-row recessed grooves 5A and 5A along the circumference of the first coupling base 3. The freely expansible and contractible spring 15 is attached to the recessed groove of the second row. One of the protruding pieces 6A and 6A provided on the second coupling base 4 is caught by pressing down using the spheres 8, and is fixed in the straight state. The lower coupling rod 2 can be rotated within the range of the gap of the extracted spheres by extracting the spheres 8. The other protruding piece 6A provided on the second coupling base 4 of the lower coupling rod 2 by the rotation of the lower coupling rod 2 pushes the freely expansible and contractible spring 15, and the force of the spring is applied to the protruding piece 6A.

FIG. 29 is a perspective view of the upper coupling rod 1, and the first coupling base 3 is formed at the lower end part. The recessed grooves 5A and 5A are formed along the circumference of the first coupling base 3. The two-row recessed grooves 5A and 5A are formed in a circular shape, and the bearing hole 18A for rotatably supporting the central shaft is bored at the center of the first coupling base 3. The fitting holes 19 and 19 for attaching to the prosthetic brace are bored on the upper coupling rod 1.

Figure 30:
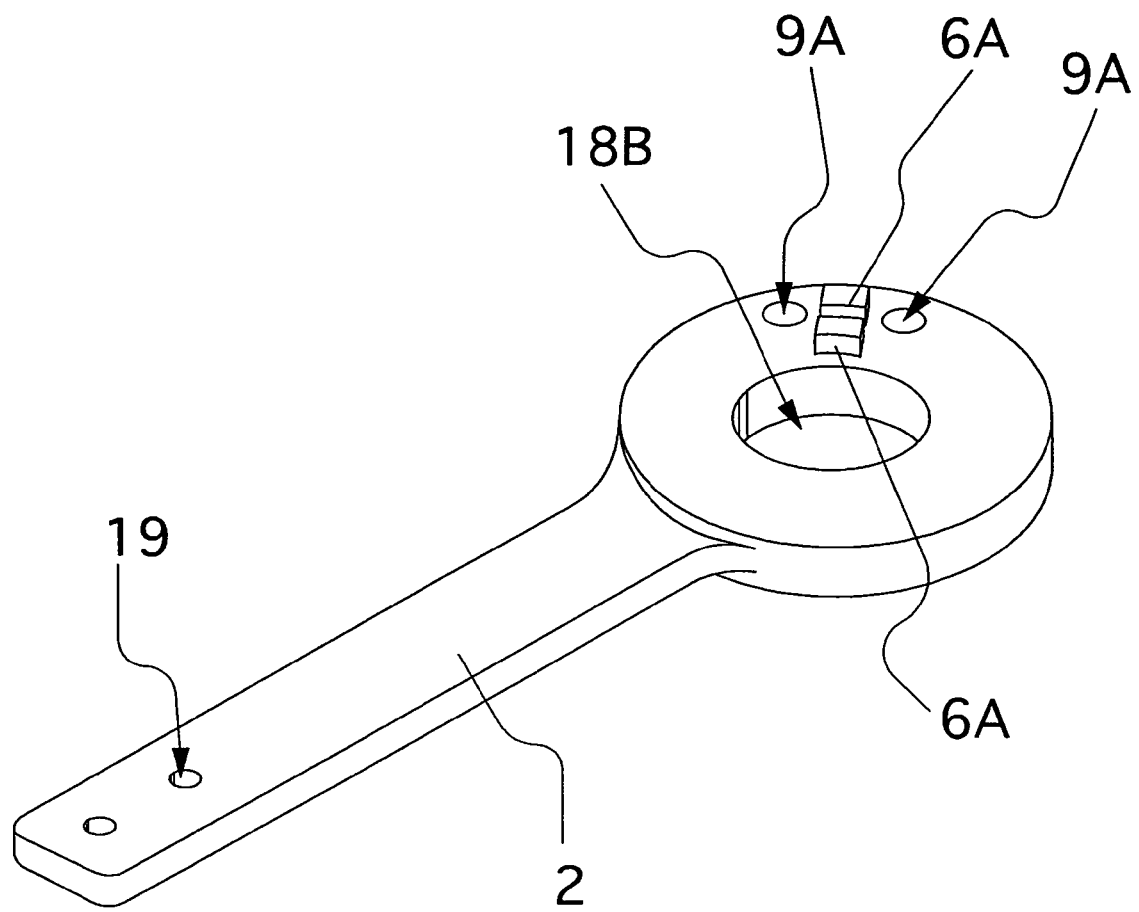
FIG. 30 is an explanatory view of a second coupling base of a joint coupling for a prosthetic brace according to Example 8 of the present invention.

FIG. 30 is a perspective view of the lower coupling rod 2, and the second coupling base 4 is formed at the upper end part. Two protruding pieces 6A and 6A are protruded on the circumferential surface of the second coupling base 4 so as to be fitted to the two-row recessed grooves 5A and 5A formed on the first coupling base 3, and the screw holes 9A and 9A for taking in and out the spheres of the recessed groove 5A of the first coupling base 3 are screwed at one of two protruding pieces 6A and 6A by the lid screw 11. The bearing hole 18B for rotatably fitting to the bearing hole 18A protruded at the central part of the first coupling base 3 is bored at the center of the second coupling base 4.

Figure 31:
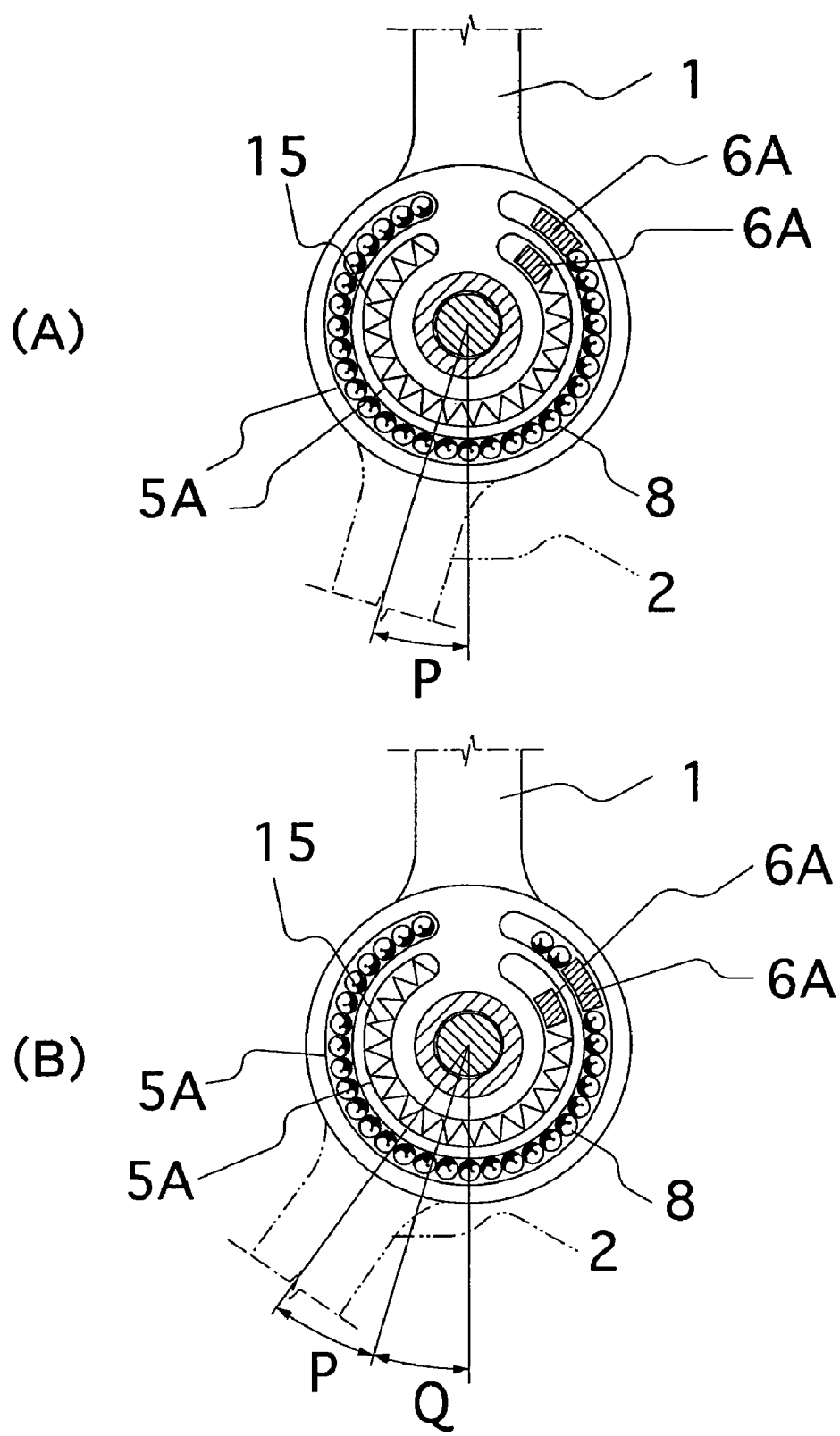
FIG. 31 is a plane sectional explanatory view showing the example of a using form of a joint coupling for a prosthetic brace according to Example 8 of the present invention.

Next, the using form of the movable region training due to the joint coupling for the prosthetic brace in Example 8 is explained in FIG. 31A and FIG. 31B.

FIG. 31A shows the example of the using form adaptable for performing the movable training within the movable region of the bending angle P of the range of the gap S obtained by extracting the spheres 8 arrayed and charged in the recessed groove 5B of the first row from the straight state of the lower coupling rod 2 to the upper coupling rod 1. The rotation of the lower coupling rod 2 is regulated by hitting the protruding piece 6A against the spheres 8 within the range of the gap S. The freely expansible and contractible spring 15 attached to the recessed groove 5A of the second row is pushed by the other protruding piece 6A, and the force of the spring is applied to the lower coupling rod 2.

FIG. 31B shows the example of the using form adaptable for performing the movable training within the movable region of the bending angle P of the range of the gap S obtained by extracting the spheres 8 arrayed and charged in the recessed groove 5B of the first row from the state of the bending angle Q of the lower coupling rod 2 to the upper coupling rod 1. The rotation of the lower coupling rod 2 is regulated by hitting the protruding piece 6A against the spheres within the range of the gap S. The freely expansible and contractible spring 15 attached to the recessed groove 5A of the second row is pushed by the other protruding piece 6A, and the force of the spring is applied to the lower coupling rod 2.

When the spheres 8 having the gap S are packed, the protruding piece 6A is caught by the spheres 8, and the lower coupling rod 2 is fixed in the state of the bending angle P+Q.

In Examples 7 and 8, when the force of the spring 15 is applied in an early movable region training, the force is strong, and thereby the spring 15 is removed and used. When the force of the spring 15 is not strong even if the force is applied as the training is repeated, the spring 15 is attached and muscle power can be increased.

Figure 32:
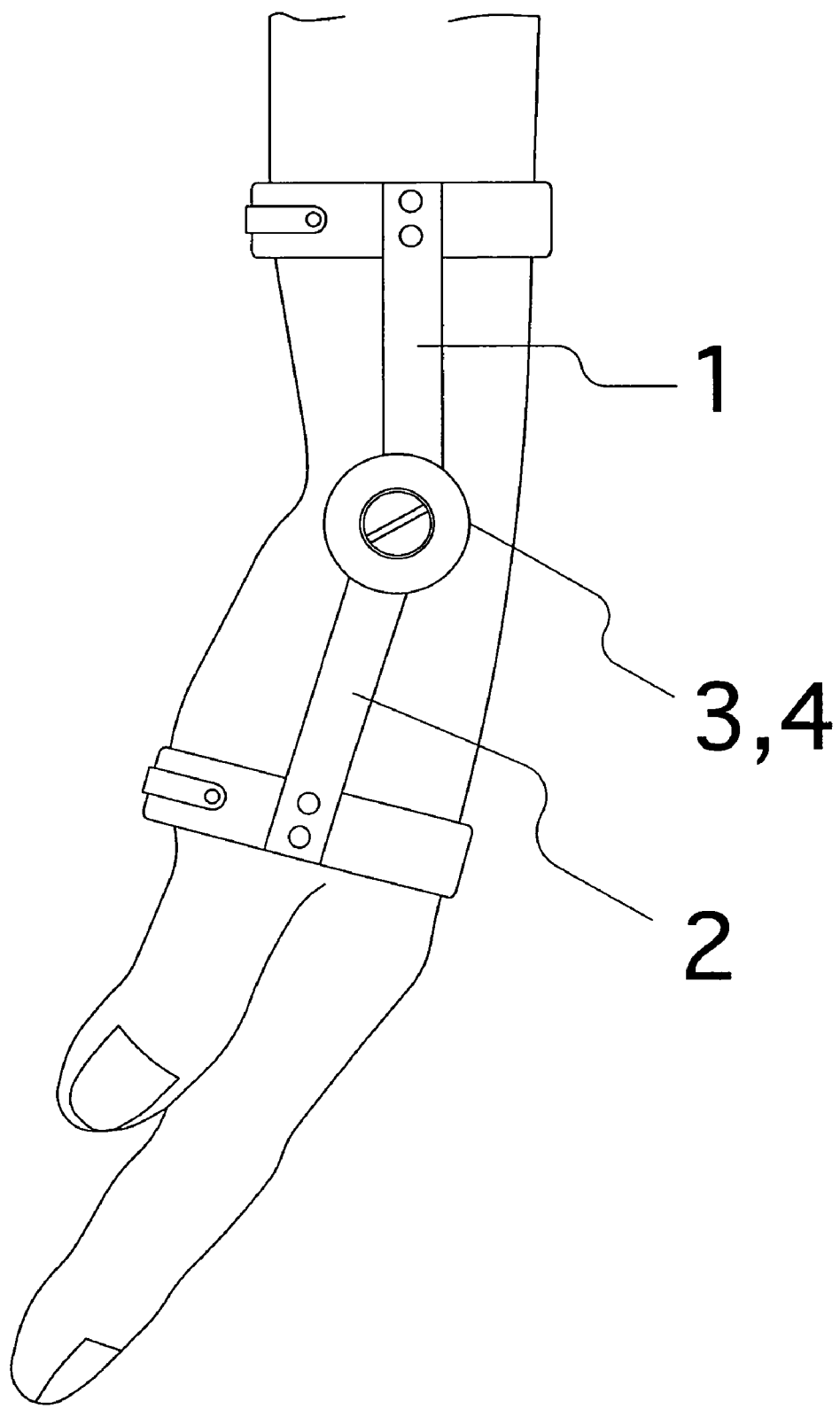
FIG. 32 is an explanatory view showing an example in which a joint coupling for a prosthetic brace according to the present invention is attached to a wrist part.

FIG. 32 shows the example in which the joint coupling for the prosthetic brace in Examples 6, 7 and 8 is attached to a wrist part.

The central parts of the first coupling base 3 and second coupling base 4 of the upper coupling rod 1 and lower coupling rod 2 are located at a joint part of a wrist part. The upper end part of the upper coupling rod 1 is fixed by the arm part of the wrist, and the lower end part of the lower coupling rod 2 is fixed by the palm part of the wrist. The joint movable range training of the stiffened wrist is performed within the movable region of the lower coupling rod 2.

At the time of attaching to the wrist part of the opposite side shown in the figure or attaching so that the wrist may be caught from the both sides, the joint coupling oppositely oriented for handling to the joint coupling shown in FIG. 32 is produced.

EXAMPLE 9

Figure 33:
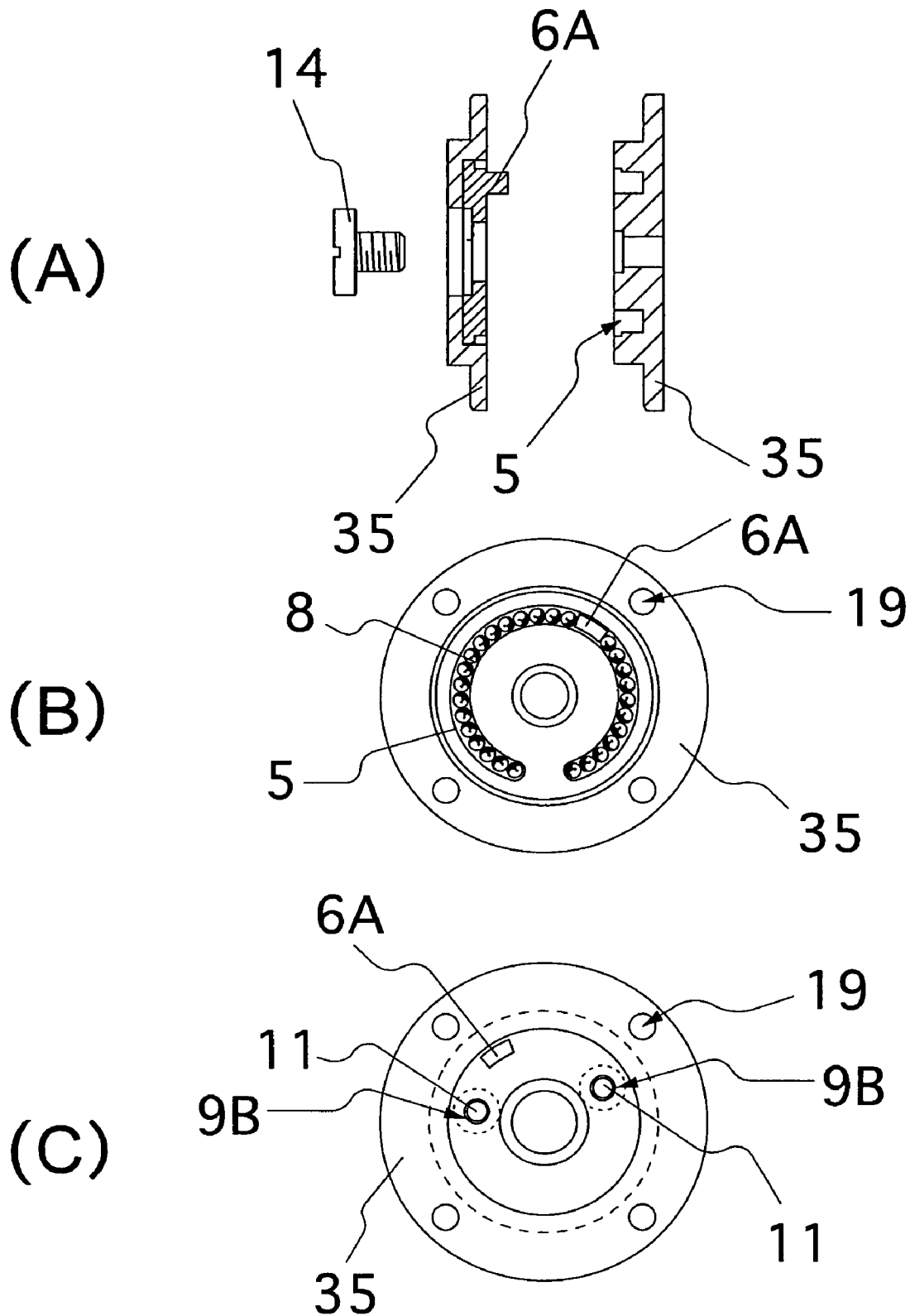
FIG. 33 is an explanatory view of a joint coupling for a prosthetic brace according to Example 9 of the present invention.

FIG. 33A and FIG. 33B show the example of application of the joint coupling for the prosthetic brace in the case of being used for the joint of the brace manufactured with plastic or the like based on the impression for the thigh, the lower thigh, the upper arm and the forearm or the like.

The fitting hole 19 is bored on the mounting flange 35 bulging out along the circumference of the first coupling base 3 and second coupling base 4. The recessed groove 5 is formed along the circumference of the first coupling base 3.

A protruding piece 6 fitted to the recessed groove 5 is formed on the circumferential surface of the second coupling base 4, and the first coupling base 3 and the second coupling base 4 are mutually pivoted in a rotatable state by a central shaft 7.

A plurality of spheres 8 formed of a superhard steel material are charged in the recessed groove 5 formed along the circumference of the first coupling base 3 in the state where the protruding piece 6 of the second coupling base 4 is sandwiched. In addition, two screw holes 9B having the diameter for freely taking in and out the spheres 8 are bored on the outer surface of the second coupling base 4 so that the screw holes 9B are communicated with the recessed groove 5. The lid screw 11 for blocking the screw hole 9B is screwed into the screw hole 9B.

EXAMPLE 10

Figure 34:
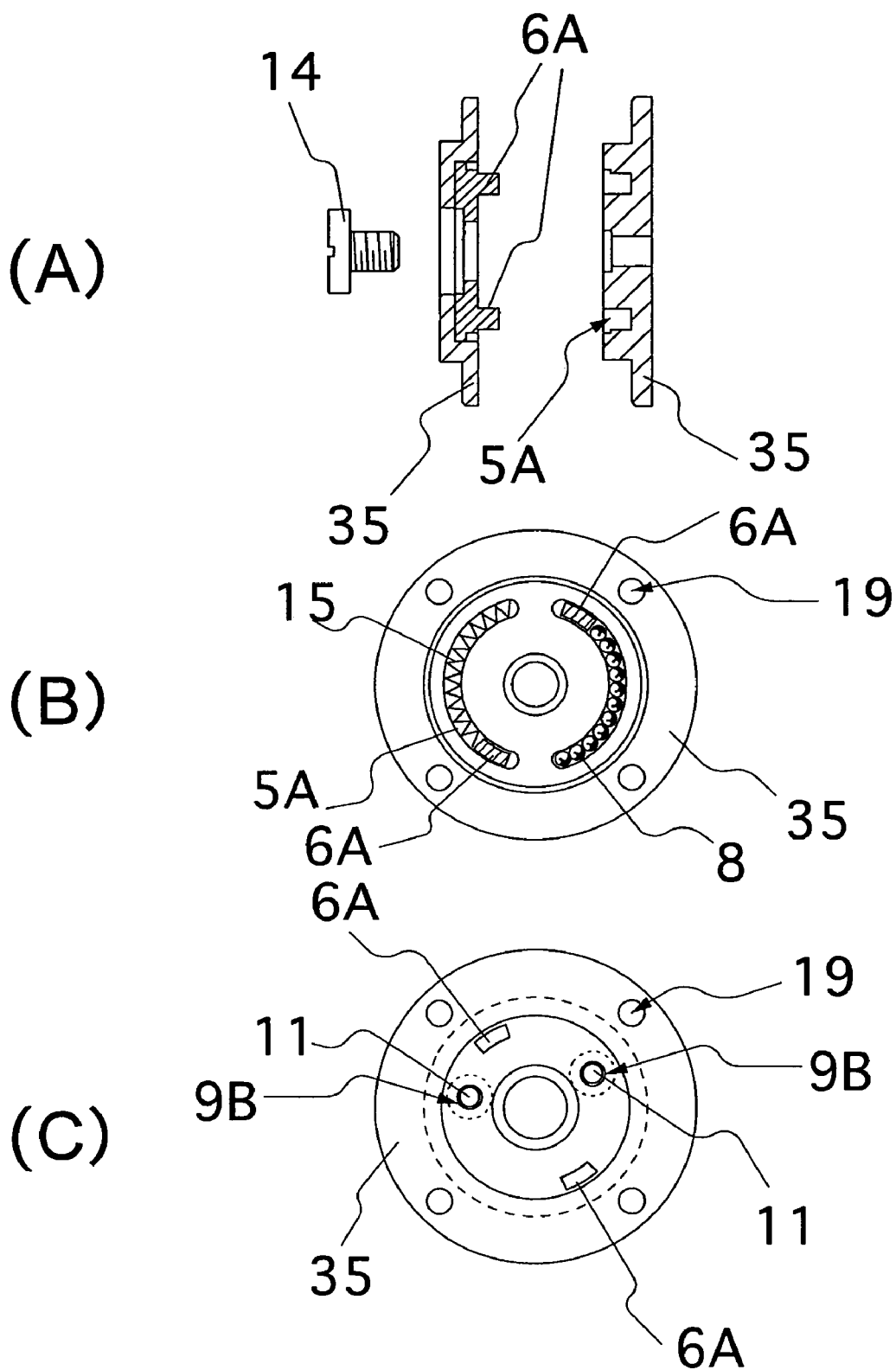
FIG. 34 is an explanatory view of a joint coupling for a prosthetic brace according to Example 10 of the present invention.

As shown in FIG. 34A and FIG. 34B, the fitting hole 19 is bored on the mounting flange 35 bulging out along the circumference of the first coupling base 3 and second coupling base 4. The recessed grooves 5A and 5A are formed by substantially half-splitting to the left and right along the circumference of the first coupling base 3.

The protruding pieces 6A and 6A are formed on the circumferential surface of the second coupling base 4 of the lower coupling rod 2. The protruding pieces 6A and 6A are fitted to the recessed grooves 5A and 5A of the first coupling base 3, and the first coupling base 3 and the second coupling base 4 are mutually pivoted in a rotatable state by the central shaft 7.

Thereby, the spheres 8 are arrayed and charged in one half of the recessed grooves 5A and 5A substantially half-split to the left and right along the circumference of the first coupling base 3. The freely expansible and contractible spring 15 is attached to the recessed groove 5A of the other half. One of the protruding pieces 6A and 6A provided on the second coupling base 4 is caught by pressing down using the sphere 8, and is fixed in the straight state. The lower coupling rod 2 can be rotated within the range of the gap of the extracted spheres by extracting the spheres 8. The other protruding piece 6A provided on the second coupling base 4 of the lower coupling rod 2 by the rotation of the lower coupling rod 2 pushes the freely expansible and contractible spring 15, and the force of the spring is applied to the protruding piece 6A.

EXAMPLE 11

Figure 35:
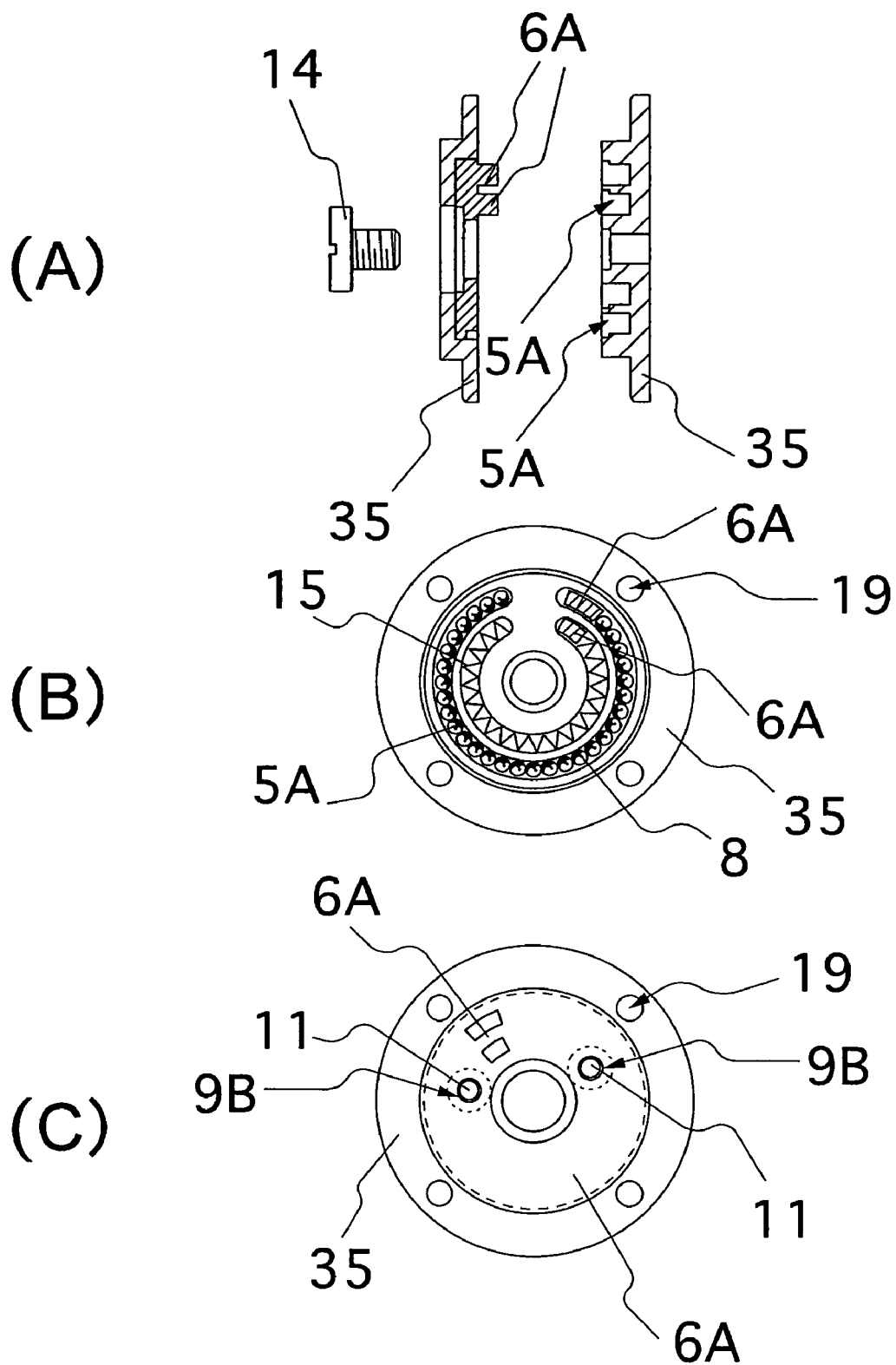
FIG. 35 is an explanatory view of a joint coupling for a prosthetic brace according to Example 11 of the present invention.

As shown in FIG. 35A and FIG. 35B, the fitting hole 19 is bored on the mounting flange 35 bulging out along the circumference of the first coupling base 3 and second coupling base 4, and the two-row recessed grooves 5A and 5A are formed along the circumference of the first coupling base 3.

The protruding pieces 6A and 6A are formed on the circumferential surface of the second coupling base 4 of the lower coupling rod 2. The protruding pieces 6A and 6A are fitted to the recessed grooves 5A and 5A of the first coupling base 3, and the first coupling base 3 and the second coupling base 4 are mutually pivoted in a rotatable state by the central shaft 7.

The spheres 8 are arrayed and charged in the recessed groove 5A of the first row of two-row recessed grooves 5A and 5A along the circumference of the first coupling base 3. The freely expansible and contractible spring 15 is attached to the recessed groove 5A of the second row. One of the protruding pieces 6A and 6A provided on the second coupling base 4 is caught by pressing down using the spheres 8, and is fixed in the straight state. The lower coupling rod 2 can be rotated within the range of the gap of the extracted spheres by extracting the spheres 8. The other protruding piece 6A provided on the second coupling base 4 of the lower coupling rod 2 by the rotation of the lower coupling rod 2 pushes the freely expansible and contractible spring 15, and the force of the spring is applied to the protruding piece 6A.

As described above, as shown in FIG. 20 and FIG. 21, the joint couplings for the prosthetic brace in Examples 9, 10 and 11 are baked to fix as the joint coupling of the upper arm brace 37 and forearm brace 38, and as the joint coupling of the thigh brace 39 and the lower thigh brace 40. When the ankled-foot brace is produced, the joint couplings for the prosthetic brace are baked to fix to the brace produced with plastic or the like as the joint coupling of the lower thigh brace 40 and foot brace 41.

Although the coil-like spring is utilized as the elastic member in Example 11, it is not necessary to use the spring. For example, any member such as rubber, urethane or silicone may be used as a material having an elastic force for repelling to pressure welding due to the protruding piece rotated in the recessed groove.

DESCRIPTION OF THE SYMBOLS 1 upper coupling rod
2 lower coupling rod
3 first coupling base
4 second coupling base
5, 5A, 5B recessed groove
6, 6A protruding piece
7 central shaft
8 sphere
9A, 9B screw hole
10 operation pin
11 lid screw
12 rotor
13 operation cover
14 stopper screw
15 spring
15A convex part
16 hole
17 insertion hole
18A, 18B, 18C bearing hole
19 fitting hole
20 outer diameter part
21 rib plate
21A and 21B curved surface part
22 coil spring
23 upper arm distant meniscus
24 upper arm proximal meniscus
25 forearm proximal meniscus
26 forearm distant meniscus
27 thigh distant meniscus
28 thigh proximal meniscus
29 lower thigh proximal meniscus
30 lower thigh distant meniscus
31 through-hole
32 projection part
33 pull type operation button
34 compressed spring
35 mounting flange
36A and 36B coupling rod
37 upper arm brace
38 forearm brace
39 thigh brace
40 lower thigh brace
41 foot brace

The invention claimed is:

1. A joint coupling for a prosthetic brace comprising:
a first coupling base having a recessed groove formed around a circumference of the first coupling base, the recessed groove being adapted to receive an array of slidable spheres;
a second coupling base rotatably coupled to the first coupling base by means of a central shaft, the second coupling base further having a protruding piece adapted to fit into the recessed groove of the first coupling base;
a rotor held rotatably between the first coupling base and the second coupling base, the rotor having at least one recessed groove; and
an operation pin which is freely insertable into the recessed groove of the first coupling base, the operation pin being adapted to control the movement of the spheres arrayed in the recessed groove of the first coupling base.

2. A joint coupling for a prosthetic brace comprising:
a first coupling base adapted to rotatably hold a rotor by means of a central shaft, the rotor having at least one recessed groove formed around a circumference of the rotor, the recessed groove being adapted to receive an array of slidable spheres;
a second coupling base rotatably coupled to the first coupling base and to the rotor by means of the central shaft, the second coupling base further having a protruding piece formed on a surface of the second coupling base, the protruding piece being adapted to fit into the recessed groove of the rotor; and
a movable operation pin adapted to lock the rotation of the rotor to the first coupling base.

3. The joint coupling for the prosthetic brace according to claim 2, wherein the recessed groove of the rotor is divided into two sections, one section being adapted to hold the spheres and the other section being adapted to hold a freely expansible and contractible elastic member.

4. A joint coupling for a prosthetic brace comprising:
a first coupling base having a recessed groove formed around a circumference of the first coupling base, the recessed groove of the first coupling base being adapted to receive an array of slidable spheres, the first coupling base further being adapted to receive a rotor having a recessed groove; and
a second coupling base rotatably coupled to the first coupling base and to the rotor by means of a central shaft, the second coupling base further having a protruding piece formed on a surface of the second coupling base and adapted to fit into the recessed groove of the first coupling base, wherein the rotation of the second coupling base is controlled by the spheres abutting against the protruding piece.

5. A joint coupling for a prosthetic brace comprising:

a first coupling base having at least one recessed groove formed around a circumference of the first coupling base, the recessed groove of the first coupling base being divided into two sections; and a second coupling base rotatably coupled to the first coupling base and to a rotor by means of a central shaft, the rotor having a recessed groove, the second coupling base further having a protruding piece formed on a surface of the second coupling base and adapted to fit into one section of the recessed groove of the first coupling base and a freely expansible and contractible elastic member mounted within and attached to the other section of the recessed groove of the first coupling base.

6. The joint coupling for the prosthetic brace according to claim 3 or 5, wherein the elastic member is formed of a freely expansible and contractible spring.

7. The joint coupling for the prosthetic brace according to claim 4 or 5, wherein the spheres arrayed in the recessed groove of the first coupling base can be freely inserted into the recessed groove manually and taken out of the recessed groove manually.

\* \* \* \* \*